US008008224B2

(12) United States Patent
Berlin et al.

(10) Patent No.: US 8,008,224 B2
(45) Date of Patent: Aug. 30, 2011

(54) ORGANOMETALLIC RUTHENIUM COMPLEXES AND RELATED METHODS FOR THE PREPARATION OF TETRA-SUBSTITUTED AND OTHER HINDERED OLEFINS

(75) Inventors: Jacob Berlin, Houston, TX (US); Robert H. Grubbs, South Pasadena, CA (US); Yann Schrodi, Pasadena, CA (US); Ian C. Stewart, Pasadena, CA (US)

(73) Assignees: Materia, Inc., Pasadena, CA (US); California Institute of Technology, Pasadena, CA (US)

( * ) Notice: Subject to any disclaimer, the term of this patent is extended or adjusted under 35 U.S.C. 154(b) by 1057 days.

(21) Appl. No.: 11/640,400

(22) Filed: Dec. 18, 2006

(65) Prior Publication Data

US 2007/0282148 A1 Dec. 6, 2007

Related U.S. Application Data

(60) Provisional application No. 60/751,225, filed on Dec. 16, 2005, provisional application No. 60/801,742, filed on May 19, 2006, provisional application No. 60/859,148, filed on Nov. 15, 2006, provisional application No. 60/853,717, filed on Oct. 19, 2006.

(51) Int. Cl.
*B01J 31/00* (2006.01)
*C07F 17/02* (2006.01)

(52) U.S. Cl. ........ 502/155; 502/167; 548/101; 548/103; 556/136; 556/21; 556/23; 526/170; 526/172

(58) Field of Classification Search .................. 502/155, 502/167; 548/101, 103; 556/126, 21, 23; 526/170, 172
See application file for complete search history.

(56) References Cited

U.S. PATENT DOCUMENTS

| 6,610,626 B2* | 8/2003 | Grubbs et al. ............... 502/155 |
| 6,759,537 B2 | 7/2004 | Grubbs et al. |
| 6,818,586 B2 | 11/2004 | Grubbs et al. |
| 6,884,859 B2* | 4/2005 | Grubbs et al. ............... 526/135 |
| 6,921,735 B2 | 7/2005 | Hoveyda et al. |
| 2004/0097745 A9 | 5/2004 | Grubbs et al. |

FOREIGN PATENT DOCUMENTS

| WO | WO 99/51344 A1 | 10/1999 |
| WO | WO 00/71554 A2 | 11/2000 |
| WO | WO 02/083742 A2 | 10/2002 |

OTHER PUBLICATIONS

PCT International Search Report and PCT Written Opinion of International Searching Authority dated May 14, 2007 for PCT International Application No. PCT/US2006/047934 filed Dec. 18, 2006.

T.J. Seiders et al., Enantioselective Ruthenium-Catalyzed Ring-Closing Metathesis, Organic Letters, 2001, pp. 3225-3228, vol. 3, No. 20.
G. Occhipinti et al., Quantitative Structure—Activity Relationships of Ruthenium Catalysts for Olefin Metathesis, *J. Am. Chem. Soc.*, 2006, 6952-6964, vol. 128, No. 21.
T.W. Funk et al., Highly Active Chiral Ruthenium Catalysts for Asymmetric Ring-Closing Olefin Metathesis, *J. Am. Chem. Soc.*, 2006, 1840-1846, vol. 128, No. 6.
J.M. Berlin et al., Highly Active Chiral Ruthenium Catalysts for Asymmetric Cross- and Ring-Opening Cross-Metathesis, *Angew. Chem. Int. Ed.*, 2006, pp. 7591-7595, vol. 45.
I.C. Stewart et al., Highly Efficient Ruthenium Catalysts for the Formation of Tetrasubstituted Olefins via Ring-Closing Metathesis, Organic Letters, 2007, pp. 1589-1592, vol. 9, No. 8.
A. Fürstner et al., Comparative Investigation of Ruthenium-Based Metathesis Catalysts Bearing N-Heterocyclic Carbene (NHC) Ligands, *Chem. Eur. J.*, 2001, pp. 3236-3253, vol. 7, No. 15.
H.E. Blackwell et al., New Approaches to Olefin Cross-Metathesis, *J. Am. Chem. Soc.*, 2000, pp. 58-71, vol. 122, No. 1.
A.K. Chatterjee et al., Synthesis of Functionalized Olefins by Cross and Ring-Closing Metatheses, *J. Am. Chem. Soc.*, 2000, pp. 3783-3784, vol. 122, No. 15; Supporting Material, pp. 1-20.
A.K. Chatterjee et al., Formal Vinyl C-H Activation and Allylic Oxidation by Olefin Metathesis, *Angew. Chem. Int. Ed.*, 2002, pp. 3171-3174, vol. 41, No. 17.
A.K. Chatterjee et al., A General Model for Selectivity in Olefin Cross Metathesis, *J. Am. Chem. Soc.*, 2003, pp. 11360-11370, vol. 125, No. 37.
J.S. Kingsbury et al., A Recyclable Ru-Based Metathesis Catalyst, *J. Am. Chem. Soc.*, 1999, pp. 791-799, vol. 121, No. 4.
S.B. Garber et al., Efficient and Recyclable Monomeric and Dendritic Ru-Based Metathesis Catalysts, *J. Am. Chem. Soc.*, 2000, pp. 8168-8179, vol. 122, No. 34.
S. Prühs et al., Preparation, Reactivity, and Structural Peculiarities of Hydroxyalkyl-Functionalized "Second-Generation" Ruthenium Carbene Complexes, *Organometallics* 2004, pp. 280-287, vol. 23, No. 2.
S.H. Hong et al., Decomposition of a Key Intermediate in Ruthenium-Catalyzed Olefin Metathesis Reactions, *J. Am. Chem. Soc.*, 2004, pp. 7414-7415, vol. 126, No. 24.
S.H. Hong et al., Prevention of Undesirable Isomerization During Olefin Metathesis, *J. Am. Chem. Soc.*, 2005, pp. 17160-17161, vol. 127, No. 49.
R.H. Grubbs, cover page and tables of contents, *Handbook of Metathesis*, vols. 1-3; Wiley VCH, Weinheim, 2003.
Office Action issued in counterpart Chinese Pat. App. No. 200680051426.3, State Intellectual Property Office of People's Republic of China, mailed Mar. 3, 2011.

* cited by examiner

*Primary Examiner* — Robert D. Harlan
(74) *Attorney, Agent, or Firm* — Nixon Peabody, LLP; Jeffrey L. Costellia

(57) ABSTRACT

The invention relates to ruthenium alkylidene complexes having an N-heterocyclic carbene ligand comprising a 5-membered heterocyclic ring having a carbenic carbon atom and at least one nitrogen atom contained within the 5-membered heterocyclic ring, wherein the nitrogen atom is directly attached to the carbenic carbon atom and is substituted by a phenyl ring, and wherein the phenyl ring has a hydrogen at either or both ortho positions and is substituted at at least one ortho or meta position. The invention also relates to an olefin metathesis reactions and particularly to the preparation of tetra-substituted cyclic olefins via a ring-closing metathesis.

14 Claims, 12 Drawing Sheets

US 8,008,224 B2

ORGANOMETALLIC RUTHENIUM COMPLEXES AND RELATED METHODS FOR THE PREPARATION OF TETRA-SUBSTITUTED AND OTHER HINDERED OLEFINS

CROSS REFERENCE TO RELATED APPLICATIONS

This application claims priority to U.S. Application 60/751,225, filed Dec. 16, 2005; U.S. Application 60/801,742, filed May 19, 2006; U.S. Application 60/859,148, filed Nov. 15, 2006; and U.S. Application 60/853,717, Oct. 19, 2006; the disclosures of which are incorporated herein by reference.

The U.S. Government has certain rights in this invention pursuant to Grant No. GM031332 awarded by the National Institutes of Health.

TECHNICAL FIELD

This invention relates generally to olefin metathesis. More particularly, the invention relates to organometallic ruthenium complexes and olefin metathesis methods using them to produce hindered olefins. The catalysts and methods of the invention have utility in the fields of catalysis, organic synthesis, and industrial chemistry.

BACKGROUND OF THE INVENTION

Olefin metathesis catalysis is a powerful technology, which in recent years has received tremendous attention as a versatile method for the formation of carbon-carbon bonds and has numerous applications in organic synthesis and polymer chemistry. R. H. Grubbs, *Handbook of Metathesis*, Vol. 2 and 3; Wiley VCH, Weinheim, 2003. The family of olefin metathesis reactions includes, but is not limited to, ring-closing metathesis (RCM), cross metathesis (CM), ring-opening metathesis polymerization (ROMP), and acyclic diene metathesis polymerization (ADMET). The success of olefin metathesis stems from the development of several well-defined transition metal complexes, such as the Schrock molybdenum catalysts and the Grubbs ruthenium catalysts. R. H. Grubbs, *Handbook of Metathesis*, Vol. 1; Wiley VCH, Weinheim, 2003. The molybdenum catalysts are generally highly active but are also highly sensitive to air, moisture, and to certain functional groups present in the olefinic substrate, the reaction solvent, or impurities. The ruthenium catalysts are much more robust than the molybdenum catalysts.

The original first-generation ruthenium catalysts were primarily bisphosphine complexes of the general formula $(PR_3)_2(X)_2Ru=CHR^a$ wherein X represents a halogen (e.g., Cl, Br, or I), R represents an alkyl, cycloalkyl, or aryl group (e.g., butyl, cyclohexyl, or phenyl), and $R^a$ represents an alkyl, alkenyl, or aryl group (e.g., methyl, $CH=CMe_2$, phenyl, etc.). Examples of these types of catalysts are described in U.S. Pat. Nos. 5,312,940, 5,969,170 and 6,111,121, which are incorporated herein by reference. While they catalyze a considerable number of olefin metathesis transformations, these bisphosphine complexes can exhibit lower activity than desired.

Second-generation metathesis catalysts with greatly increased activity have now been prepared by replacing one of the phosphine ligands with an N-heterocyclic carbene (NHC) ligand to give complexes of the general formula $(L)(PR_3)(X)_2Ru=CHR^a$ wherein L represents an NHC ligand such as 1,3-dimesitylimidazole-2-ylidene (IMES) and 1,3-dimesityl-4,5-dihydroimidazol-2-ylidene (sIMES), X represents a halogen (e.g., Cl, Br, or I), R represents an alkyl, cycloalkyl, or aryl group (e.g., butyl, cyclohexyl, or phenyl), and $R^a$ represents an alkyl, alkenyl, or aryl group (e.g., methyl, $CH=CMe_2$, phenyl, etc.). Examples of these types of NHC ligands and catalysts are described in PCT publications WO 99/51344 and WO 00/71554, which are incorporated herein by reference. Further examples of the synthesis and reactivity of some of these active ruthenium complexes are reported by A. Fürstner, L. Ackermann, B. Gabor, R. Goddard, C. W. Lehmann, R. Mynott, F. Stelzer, and O. R. Thiel, *Chem. Eur. J.*, 2001, 7, No. 15, 3236-3253; Blackwell H. E., O'Leary D. J., Chatterjee A. K., Washenfelder R. A., Bussmann D. A., Grubbs R. H. *J. Am. Chem. Soc.* 2000, 122, 58-71; Chattetjee A. K., Morgan J. P., Scholl M., Grubbs R. H. *J. Am. Chem. Soc.* 2000, 122, 3783-3784; Chatterjee A. K., Grubbs R. H. *Angew. Chem. Int. Ed.* 2002, 41, 3171-3174; Chatterjee A. K., Choi T. L., Sanders D. P., Grubbs R. H. *J. Am. Chem. Soc.* 2003, 125, 11360-11370. The disclosure of these articles are incorporated herein by reference.

Despite such advances in the development of olefin metathesis catalysts, the metathesis of hindered olefins remains difficult and certain metathesis reactions to form tetra-substituted olefins proceed slowly and in low to moderate yields. A need exists, therefore, for metathesis catalysts capable of efficiently and effectively carrying out metathesis reactions with hindered olefins. The ruthenium catalysts of this invention answer that need.

BRIEF DESCRIPTION OF THE DRAWINGS

Further features and advantages of the organometallic complexes, methods and reaction systems herein disclosed will become apparent from the following detailed description, taken in combination with the appended drawings, in which:

FIG. 20 is a graph of the conversion over time for the RCM reaction of 15 in Example 29 for catalyst 6a.

FIG. 21 is a graph of the conversion over time for the RCM reaction of 13 in Example 29 for catalyst 6a.

FIG. 22 is a graph of the conversion over time for the RCM reaction of 15 in Example 29 for catalyst 7a.

FIG. 23 is a graph of the conversion over time for the RCM reaction of 13 in Example 29 for catalyst 7a.

SUMMARY OF THE INVENTION

Figure 1:
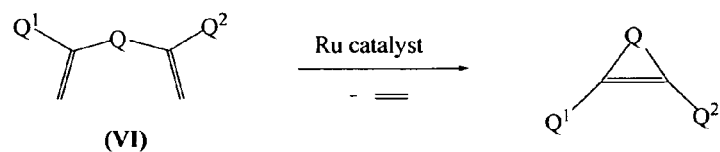
FIG. 1 shows a reaction scheme illustrating an exemplary embodiment of the method for preparing a cyclic tetra-substituted olefin via ring-closing metathesis herein disclosed.

The invention relates to ruthenium alkylidene complexes having an N-heterocyclic carbene ligand comprising a 5-membered heterocyclic ring having a carbenic carbon atom and at least one nitrogen atom contained within the 5-membered heterocyclic ring, wherein the nitrogen atom is directly attached to the carbenic carbon atom and is substituted by a phenyl ring, and wherein the phenyl ring has a hydrogen at either or both ortho positions and is substituted at least one ortho-, or meta-position.

In a preferred embodiment, the invention relates to N-heterocyclic carbene (NHC) ruthenium olefin metathesis catalyst of formula (I):

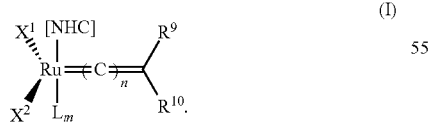
(I)

The catalysts of formula (I) contain the NHC ligand as well as the other ligands shown. In formula (I), $X^1$ and $X^2$ are independently anionic ligands; "n" is 0, 1, or 2; $R^9$ and $R^{10}$ are each independently hydrogen or a substituted or unsubstituted substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl; L is a neutral 2-electron donor ligand; and "m" is 1 or 2. $R^9$ and $R^{10}$ may optionally be linked together to form a cyclic structure via one of the substituents mentioned above. L may optionally be linked to $R^{10}$ to form a chelating carbene ligand, however, the formation of the chelating carbene ligand only occurs when n is 0. When "m" is a heteroarene ligand. Preferably, the heteroarene ligand 2, L is pyridine or substituted pyridine, which forms a (bis)pyridine catalyst. See Example 28, depicting a (bis)pyridine catalyst.

Preferred NHC ligands for the ruthenium catalysts of the invention are those of formulas (II)-(V):

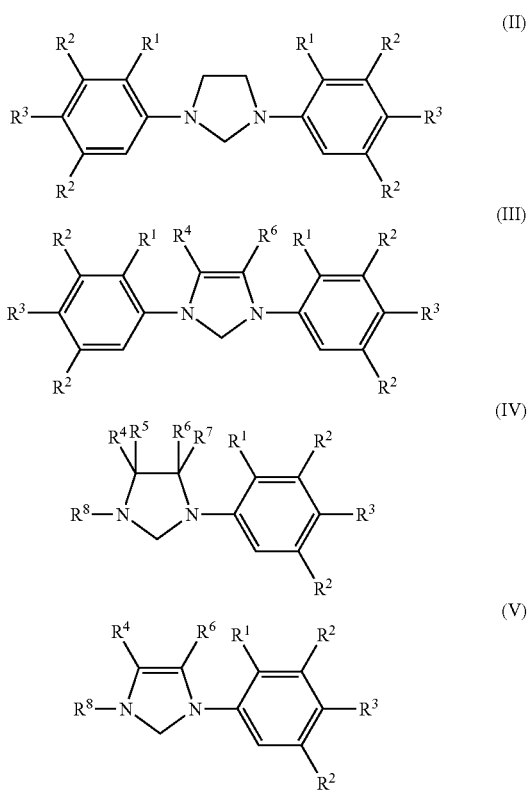

In formulas (II)-(V), $R^1$, $R^2$, and $R^3$ are either:
a) each $R^1$ is independently a primary or secondary $C_1$-$C_4$ alkyl group; each $R^2$ is independently H, a substituted or unsubstituted $C_1$-$C_{10}$ alkyl group, substituted or unsubstituted phenyl, substituted or unsubstituted naphthyl, or substituted or unsubstituted anthracenyl; and each $R^3$ is independently H, a substituted or unsubstituted $C_1$-$C_8$ alkyl group, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; or
b) $R^1$ is H; each $R^2$ is independently H, a substituted or unsubstituted $C_1$-$C_8$ alkyl group, substituted or unsubstituted phenyl, substituted or unsubstituted naphthyl, or substituted or unsubstituted anthracenyl; and $R^3$ is independently H, a substituted or unsubstituted $C_1$-$C_8$ alkyl group, substituted or unsubstituted phenyl, substituted or unsubstituted naphthyl, or substituted or unsubstituted anthracenyl or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; with the provisos that both $R^2$ substituents on the same phenyl ring are not H.

$R^4$ and $R^6$ are each independently H, a substituted or unsubstituted $C_1$-$C_8$ alkyl group, substituted or unsubstituted aryl, or in formulas (III) and (V) together with the carbons carrying them form a substituted or unsubstituted, fused 4-8 membered carbocylic ring or a substituted or unsubstituted, fused aromatic ring, preferably a fused phenyl ring. $R^5$ and $R^7$ are independently H, a substituted or unsubstituted $C_1$-$C_8$ alkyl group. $R^8$ is a $C_1$-$C_{12}$ alkyl or a $C_3$-$C_{12}$ cycloalkyl.

Another embodiment of the invention relates to an olefin metathesis reaction which contacts an olefin with an N-heterocyclic carbene (NHC) ruthenium olefin metathesis catalyst of the invention under metathesis conditions. The catalysts of the invention may be used in, for example, ring-closing metathesis (RCM), cross metathesis (CM), ring-opening metathesis polymerization (ROMP), and acyclic diene metathesis polymerization (ADMET).

A further embodiment of the invention relates to the preparation of tetra-substituted cyclic olefins via a ring-closing metathesis. In this embodiment, the invention provides a ring-closing metathesis method to prepare a tetra-substituted cyclic olefin. In the method, an olefinic compound having at least two terminal olefins which are substituted at the beta-carbon of each terminal olefin is contacted with an N-heterocyclic carbene (NHC) ruthenium olefin metathesis catalyst of the invention under metathesis conditions to form a cyclic tetra-substituted olefin.

DETAILED DESCRIPTION OF THE INVENTION

The invention relates to N-heterocyclic carbene (NHC) ruthenium olefin metathesis catalysts. Advantageously, the catalysts of the invention display greater efficiency/activity than current olefin metathesis catalysts for catalyzing ring-closing metathesis (RCM) reactions to form tetra-substituted cyclic olefins. The catalysts also perform the other known metathesis reactions in the family of metathesis reactions discussed above. The catalysts are also particularly useful in cross-metathesis to prepare tri-substituted olefins, and di-substituted olefins that are further substituted at the allylic carbon. The N-heterocyclic carbene (NHC) ruthenium olefin metathesis catalysts of the invention have the following general formula (I):

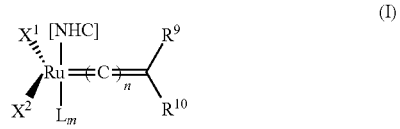

(I)

In the catalysts of formula (I), $X^1$ and $X^2$ are independently anionic ligands. Preferably, $X^1$ and $X^2$ are halide, or one of the following groups: $C_1$-$C_{20}$ alkyl, aryl, $C_1$-$C_{20}$ alkoxide, aryloxide, $C_3$-$C_{20}$ alkyldiketonate, aryldiketonate, $C_1$-$C_{20}$ carboxylate, arylsulfonate, $C_1$-$C_{20}$ alkylsulfonate, $C_1$-$C_{20}$ alkylthio, $C_1$-$C_{20}$ alkylsulfonyl, or $C_1$-$C_{20}$ alkylsulfinyl. Optionally, $X^1$ and $X^2$ may be substituted with one or more moieties selected from the group consisting of $C_1$-$C_{10}$ alkyl, $C_1$-$C_{10}$ a alkoxy, and aryl which in turn may each be further substituted with one or more groups selected from halogen, $C_1$-$C_5$ alkyl, $C_1$-$C_5$ alkoxy, and phenyl. In more preferred embodiments, $X^1$ and $X^2$ are halide, benzoate, $C_1$-$C_5$ carboxylate, $C_1$-$C_5$ alkyl, phenoxy, $C_1$-$C_5$ alkoxy, $C_1$-$C_5$ alkylthio, aryl, and $C_1$-$C_5$ alkyl sulfonate. As discussed below, the other ligands in a catalyst of the invention, when substituted, may also contain such substituents. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, $X^1$ and $X^2$ are each chloride.

The variable "n" defines the number of successive double bounds in the alkylidene substituted by $R^9$ and $R^{10}$. The variable "n" is 0, 1 or 2. Preferably, "n" is 0.

$R^9$ and $R^{10}$ are each independently hydrogen or a substituted or unsubstituted group selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ 20 alkylsulfonyl and $C_1$-$C_{20}$ alkylsulfinyl. Optionally, each of the $R^9$ or $R^{10}$ substituent group may be substituted with one or more moieties selected from the group consisting of $C_1$-$C_{10}$ alkyl, $C_1$-$C_{10}$ alkoxy, and aryl which in turn may each be further substituted with one or more groups selected from a halogen, a $C_1$-$C_5$ alkyl, $C_1$-$C_{15}$ alkoxy, and phenyl. Moreover, $R^9$ and $R^{10}$, as well as any other of the catalyst ligands, may further include one or more functional groups as long as they do not defeat the activity of the catalyst. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. $R^9$ and $R^{10}$ may optionally be linked together to form a cyclic structure via one of the substituents mentioned above.

In preferred embodiments of these catalysts, the $R^9$ substituent is hydrogen, $C_1$-$C_5$ alkyl or aryl and the $R^{10}$ substituent is selected from the group consisting of $C_1$-$C_{20}$ alkyl, $C_2$-$C_{20}$ alkenyl, and aryl. In even more preferred embodiments, the $R^{10}$ substituent is phenyl or vinyl, optionally substituted with one or more moieties selected from the group consisting of $C_1$-$C_5$ alkyl, $C_1$-$C_5$ alkoxy, phenyl, and a functional group. In especially preferred embodiments, $R^{10}$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^{10}$ substituent is phenyl or —C=C(CH_3)_2$.

L may be any neutral 2-electron donor ligand known in the art. The variable "m" defines the number of neutral donor ligands, L. The variable "m" is 1 or 2 and preferably 1. When "m" is 1, L is any neutral 2-electron donor ligand. L may be linked to $R^{10}$ forming a chelating carbene ligand when "n" is zero. When "m" is 2, L is a heteroarene ligand such as pyridine or substituted pyridine. See U.S. Pat. Nos. 6,759,537 and 6,818,586, herein incorporated by reference in their entirety; for examples of suitable heteroarene ligands. Preferably, the heteroarene ligand is pyridine or substituted pyridine.

In a preferred embodiment, L is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L is a phosphine of the formula PR'R"R'", where R', R", and R'" are each independently aryl; $C_1$-$C_{10}$ alkyl (in particular, a primary or secondary alkyl); or $C_3$-$C_6$ cycloalkyl. In the most preferred embodiments, L is selected from the group consisting of P(cyclohexyl)$_3$, P(cyclopentyl)$_3$, P(isopropyl)$_3$, and P(phenyl)$_3$.

In a preferred embodiment, L may be linked to R$^{10}$ forming a chelating carbene ligand. When forming a chelating carbene ligand, n is zero. The L portion of the chelating carbene ligand is still a 2-electron donor ligand when linked to R$^{10}$. L may or may not be linked to R$^{10}$ through a spacer moiety. U.S. Pat. No. 6,921,735 describes chelating carbene ligands and is incorporated herein by reference for examples of how the ligand and R substituent on the carbene can be linked through various spacer moieties. The spacer moiety may be substituted or unsubstituted. Preferred catalysts of the invention where L and R$^{10}$ are linked include the following:

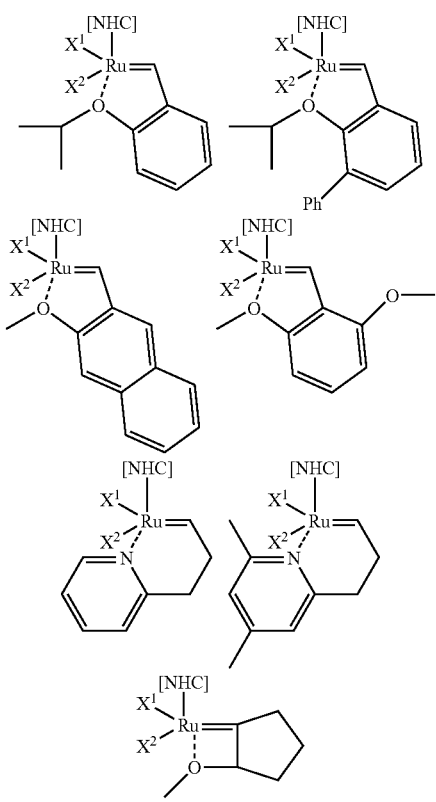

Examples of ruthenium complexes with chelating carbene ligands, ligands linking the L ligand and the R$^{10}$ substitutent, are also described in Kingsbury, J. S.; Harrity, J. P. A.; Bonitatebus, P. J., Jr.; Hoveyda, A. H. *J. Am. Chem. Soc.* 1999, 121, 791 and Garber, S. B.; Kingsbury, J. S.; Gray, B. L.; Hoveyda, A. H. *J. Am. Chem. Soc.* 2000, 122, 8168. Preferably, R$^{10}$ is linked to L via spacer group being 2-5 atoms in length between L and R$^{10}$, for example via an alkyl group, a cycloloalkyl group, or an aryl group. A preferred spacer group is a substituted or unsubstituted phenyl group.

In the catalysts of the invention there is an N-heterocyclic carbene (NHC) ligand which is a ligand comprising a 5-membered NHC ring, i.e., a carbene where the carbenic carbon atom is contained within a 5-membered cyclic structure. The 5-membered cyclic structure that contains the carbenic carbon atom also contains at least one nitrogen atom directly attached to the carbenic carbon atom and that nitrogen atom is substituted by a phenyl ring. The phenyl ring itself has a hydrogen (i.e. is unsubstituted) at either or both ortho positions but substituted at least one ortho-, or meta-position.

As described in the preferred embodiments below, the 5-membered NHC ring may, in some circumstances, be part of a polycyclic group and the phenyl ring may be part of a polycyclic aryl group. Preferred NHC ligands are those of those of formulas (II)-(V):

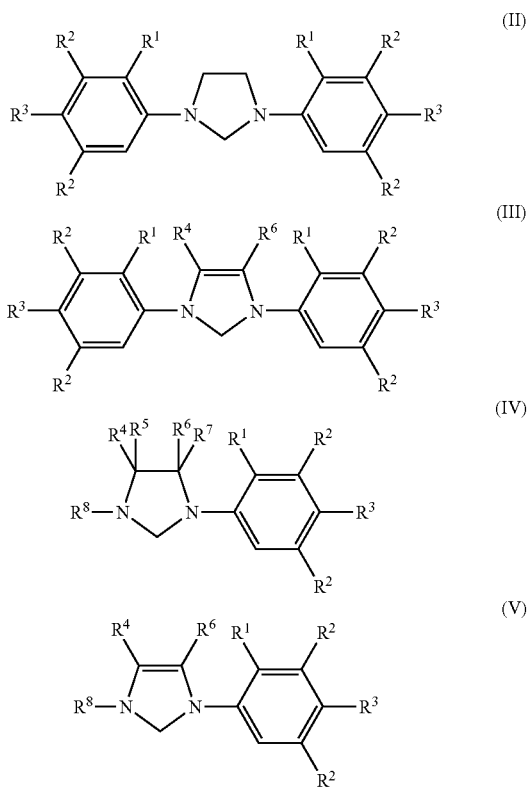

In the preferred NHC ligands of formulas (II)-(V) there are two preferred combinations of R$^1$, R$^2$, and R$^3$ which define the substitution pattern on the phenyl ring bound to the nitrogen atom bound to the carbene carbon. Note that in the NHC ligands used in the complexes of the invention, at least one ortho position on the phenyl ring is a hydrogen. In other words, the phenyl ring is always unsubstiued at least one ortho position. In certain preferred combinations of R$^1$, R$^2$, and R$^3$ both ortho positions are hydrogen and, therefore, unsubstituted. The preferred combinations of R$^1$, R$^2$, and R$^3$ are:

a) each R$^1$ is independently a primary or secondary C$_1$-C$_4$ alkyl group; each R$^2$ is independently H, a substituted or unsubstituted C$_1$-C$_{10}$ alkyl group, substituted or unsubstituted phenyl, substituted or unsubstituted naphthyl, or substituted or unsubstituted anthracenyl; and each R$^3$ is independently H, a substituted or unsubstituted C$_1$-C$_8$ alkyl group, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; or b) R$^1$ is H; each R$^2$ is independently H, a substituted or unsubstituted C$_1$-C$_8$ alkyl group, substituted or unsubstituted phenyl, substituted or unsubstituted naphthyl, or substituted or unsubstituted anthracenyl; and R$^3$ is independently H, a substituted or unsubstituted C$_1$-C$_8$ alkyl group, substituted or unsubstituted phenyl, substituted or unsubstituted naphthyl, or substituted or unsubstituted anthracenyl or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; with the proviso that both $R^2$ substituents on the same phenyl ring are not H.

In combination a), $R^1$ is preferably methyl, ethyl, or isopropyl. Each separate $R^2$ is preferably H, iso-butyl, tert-butyl, neopentyl, neohexyl, or phenyl and is most preferably H. Each $R^3$ is preferably H, iso-butyl, tert-butyl, neopentyl, neohexyl, or phenyl and is most preferably H.

In combination b), when $R^1$ and $R^3$ are H and $R^2$ is one of the listed substituents, the phenyl group of the NHC ligand is bis-meta substituted; and when $R^1$ and $R^3$ and $R^2$ are each one of the listed substituents, the phenyl group of the NHC ligand is bis-meta and para-substituted. Because $R^1$ is H, the proviso within combination b), that both $R^2$'s on the same phenyl ring are H, exclude those NHC ligands having an unsubstituted phenyl or a, para-substituted phenyl. $R^2$ is preferably a secondary or tertiary $C_3$-$C_{10}$ alkyl or aryl; more preferably, iso-butyl, tert-butyl, neopentyl, neohexyl, or phenyl and most preferably tert-butyl. $R^3$ is preferably H, iso-butyl, tert-butyl, neopentyl, neohexyl, or phenyl and is most preferably H.

In the NHC ligands used in the complexes of the invention, $R^4$ and $R^6$ are each independently H, a substituted or unsubstituted $C_1$-$C_8$ alkyl group, substituted or unsubstituted aryl, or in formulas (III) and (V), together with the carbons carrying them, form a substituted or unsubstituted, fused 4-8 membered carbocyclic ring or a substituted or unsubstituted, fused aromatic ring. Preferably $R^4$ and $R^6$ are H, $C_1$-$C_4$ alkyl, or fused cyclolhexyl or phenyl (in formulas (III) and (V)). $R^5$ and $R^7$ are independently H, a substituted or unsubstituted $C_1$-$C_8$ alkyl group and preferably H or $C_1$-$C_4$ alkyl.

In the NHC ligands of formulas (IV) and (V), $R^8$ is a $C_1$-$C_{12}$ alkyl or a $C_3$-$C_{12}$ cycloalkyl. Preferably $R^8$ is methyl, ethyl, or iso-propyl and most preferably is methyl.

Examples of preferred NHC ligands for catalysts of the invention are shown below:

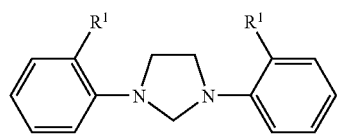

where $R^1$=methyl, ethyl, propyl, isopropyl

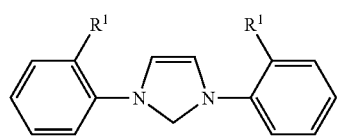

where $R^1$=methyl, ethyl, propyl, isopropyl

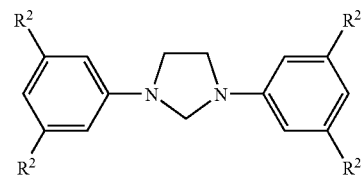

where $R^2$=tert-butyl

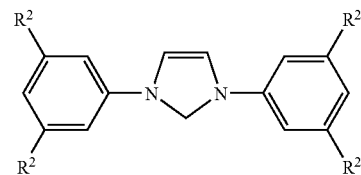

where $R^2$=tert-butyl

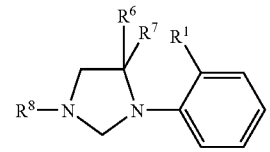

where $R^1$=methyl, ethyl, propyl, isopropyl; $R^6$=$R^7$=hydrogen or methyl; and $R^8$=methyl.

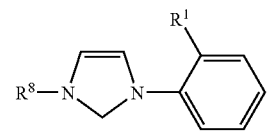

where $R^1$=methyl, ethyl, propyl, isopropyl; and $R^8$=methyl.

Synthesis of NHC Ligands

The NHC ligands of formulas (II) and (III) used to form the catalysts of the invention may be prepared from aniline derivatives using known procedures used to prepare other known NHC ligands, such as the second generation metathesis catalysts discussed above. The aniline derivative used bears the desired substituents and substitution pattern. Typically, two equivalents of the aniline derivative are reacted with glyoxal to begin the synthesis. Use of the two equivalents of the same aniline gives a symmetric NHC ligand. Asymmetric NHC ligands can be prepared by using two different aniline derivatives. For asymmetric NHC ligands, the aniline derivatives are preferably reacted with the glyoxal in two separate steps to avoid a mixture of products.

Alternatively, NHC ligands of formulas (II) and (III) maybe prepared by reacting two equivalents of the same aniline with oxalyl chloride. Subsequent reduction of the product bisamide yields a diamine that can be transformed by techniques known in the art to a salt, which is a direct NHC ligand precursor. For differentially substituted NHC ligands, typically, one aniline is reacted with ethyl chlorooxoacetate and the product of that reaction is reacted with the second aniline. Again, reduction of the product bisamide yields a diamine that can be transformed by techniques known in the art to a salt, which is a direct NHC ligand precursor. Examples of the preparation of NHC ligands of formulas (II) and (III) are shown below in Examples 1, 6, 12, 13, and 17.

Salt precursors of NHC ligands of formulas (IV) and (V) can be prepared by a procedure similar to that described by Blechert and coworkers in *Organometallics* 2006, 25, 25-28: first a diamine $R^8NH—(CH_2)_2—NH_2$ is arylated under Buchwald-Hartwig conditions to give $R^8NH—(CH_2)_2—NH[C_6HR^1(R^2)_2R^3]$, which is then reacted with triethylorthoformate in the presence of $NH_4BF_4$ to give the $HBF_4$ salt precursor of NHC ligands of formula (IV). Salt precursors of NHC ligands of formula (V) can be prepared by reacting N-(substituted phenyl)imidazole (where substituted phenyl is $C_6HR^1(R^2)_2R^3$) with an alkyl halide (where alkyl is $R^8$) according to the procedure described by Fürstner and coworkers in *Organometallics* 2004, 23, 280-287. The NHC ligands of formulas (IV) and (V) may be prepared by deprotonation of their corresponding NHC salts.

Synthesis of Catalysts

The ruthenium catalysts of the invention may be prepared using methods known in the art. In general, the catalysts of the present invention are prepared via a ligand exchange reaction, for example, by substituting an NHC ligand for one of the neutral electron donor ligands in a first generation ruthenium carbene complexes (discussed above). For example, a catalyst of the invention can be prepared by replacing a phosphine ligand in a complex of the general formula $(PR_3)_2(X)_2Ru=CHR$ with an NHC ligand described above. As discussed in the Background of the Invention, these synthetic procedures are known in the art. Examples 2, 7, 11, 12, 14, and 15 illustrate preparation of ruthenium catalysts of the invention by this method.

Metathesis Reactions

The ruthenium catalysts of the invention are particularly efficient olefin metathesis catalysts. Accordingly, one embodiment of the invention is an olefin metathesis reaction which contacts an olefin with an N-heterocyclic carbene (NHC) ruthenium olefin metathesis catalyst of the invention under metathesis conditions. The catalysts of the invention may be used in, for example, ring-closing metathesis (RCM), cross metathesis (CM), self metathesis (which is a type of cross metathesis), ring-opening metathesis polymerization (ROMP), and acyclic diene metathesis polymerization (ADMET).

The metathesis conditions for the catalysts of the invention are the same as those used in other olefin metathesis reactions and with other known olefin metathesis catalysts. Generally speaking, the olefin metathesis reactions are run at a temperature ranging from about 10° C. to about 70° C. and for a time period ranging from about 5 minutes to about 24 hours. The catalysts of the invention may be used in the same amounts as know for other olefin metathesis catalysts. Typically, about 1 to about 10 mol % of the catalyst is used and more often about 5 mol %.

The ruthenium catalysts of the invention are particularly useful in metathesis reactions for the production of tetra-substituted cyclic olefins. The catalysts of the invention have significantly increased efficiency/activity for the preparation of tetra-substituted cyclic olefins via olefin metathesis. To answer the need for more efficient preparation of such olefins another embodiment of the invention is a ring-closing metathesis method to prepare a tetra-substituted cyclic olefin. The method contacts an olefinic compound having at least two terminal olefins which are substituted at the beta-carbon of each terminal olefin with an N-heterocyclic carbene (NHC) ruthenium olefin metathesis catalyst of the invention under metathesis conditions to form a cyclic tetra-substituted olefin.

A preferred group of olefinic compounds are those which have a structure according to formula (VI):

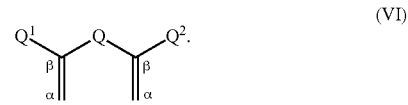

In formula (VI), Q is selected from hydrocarbylene, substituted hydrocarbylene, heteroatom-containing hydrocarbylene, and substituted heteroatom-containing hydrocarbylene. $Q^1$ and $Q^2$ are independently selected from hydrogen, hydrocarbyl, substituted hydrocarbyl, heteroatom-containing hydrocarbyl, substituted heteroatom-containing hydrocarbyl, and other groups such as halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy. In the preparation of hindered cyclic olefins, both $Q^1$ and $Q^2$ cannot both be hydrogen and, more preferably, are both not hydrogen.

The catalysts are useful in cross-metathesis to prepare tri-substituted olefins, and di-substituted olefins which are further substituted at the allylic carbon. Accordingly, an embodiment of the invention relates to a cross-metathesis reaction in which an N-heterocyclic carbene (NHC) ruthenium olefin metathesis catalyst of the invention contacts two olefins under metathesis conditions. The first olefin is monosubstituted at the β-carbon and either unsubstituted or monosubstituted at the α-carbon. The second olefin is either disubstituted at the β-carbon or monosubstituted at the β-carbon but also has further substitution at the allylic carbon. Both olefins are either monosubstituted or unsubstituted at the α-carbon.

Examples of tri-substituted olefins are those having the formula $Q^1Q^2C=CHQ^3$. $Q^1$, $Q^2$, and $Q^3$ are independently selected from hydrocarbyl, substituted hydrocarbyl, heteroatom-containing hydrocarbyl, substituted heteroatom-containing hydrocarbyl, and other groups such as halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy. Any number of $Q^1$, $Q^2$, and $Q^3$ may also be linked as part of a cyclic olefin.

Di-substituted olefins are represented, for example, by the formula $Q^1Q^2C=CH_2$ or $Q^1HC=CHQ^2$. $Q^1$ and $Q^2$ are independently selected from hydrocarbyl, substituted hydrocarbyl, heteroatom-containing hydrocarbyl, substituted heteroatom-containing hydrocarbyl, and other groups such as halide, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy. $Q^1$ and $Q^2$ may also be linked in the case of cyclic olefins.

The formula $Q^1HC=CHCQ^2Q^3Q^4$ is representative of exemplary di-substituted olefins having further substitution at the allylic carbon. In this formula $Q^1$, $Q^2$, $Q^3$, and $Q^4$ are independently selected from hydrogen, hydrocarbyl, substituted hydrocarbyl, heteroatom-containing hydrocarbyl, substituted heteroatom-containing hydrocarbyl, and other groups such as halide, hydroxyl, sulfhydryl, cyano, cyanato, thiocyanato, amino, nitro, nitroso, sulfo, sulfonato, boryl, borono, phosphono, phosphonato, phosphinato, phosphino, and silyloxy, provided that at least two of $Q^2$, $Q^3$ and $Q^4$ are different from hydrogen. $Q^1$, $Q^2$, $Q^3$, and $Q^4$ can be linked when the olefin is a cyclic olefin.

The term "hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups such as discussed above, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups discussed above, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

EXAMPLES

Example 1

Ortho Substituted NHC Ligand Synthesis

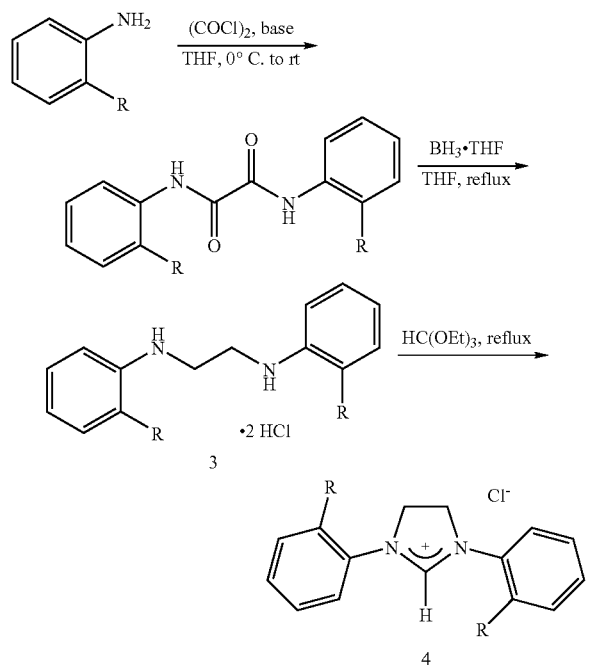

General procedure for the preparation of N,N'-Diaryl oxamides. Oxalyl chloride (4.36 mL, 50 mmol) was added dropwise to a stirred solution of aniline $C_6H_4RNH_2$ (100 mmol, 2 equiv) and base (100 mmol, 2 equiv) in THF (200 mL) at 0° C. Triethylamine or aq. NaOH may be used as bases for this reaction. Upon addition, the reaction was allowed to warm up to room temperature (r.t.) and stirred for 1 h. The reaction mixture was then concentrated in vacuo and diluted with water (100 mL). The white precipitate was collected by filtration, washed with dilute HCl (100 mL), water (2×100 mL), and dried in vacuo. The following N,N'-diaryl oxamides were prepared by this procedure:

N,N'-Bis(o-tolyl) oxamide. Obtained in a 98% yield as a white solid. $^1$H NMR (300 MHz, CDCl$_3$): δ 9.38 (s, 2H), 8.09 (d, $^3J_{HH}$=7.8 Hz, 2H), 7.31-7.12 (m, 6H), 2.39 (s, 6H).

N,N'-Bis(2-ethylphenyl)oxamide. Obtained in a 71% yield as a white solid.

N,N'-Bis(2-isopropylphenyl)oxamide. Obtained in a 60% yield as a white solid. $^1$H NMR (300 MHz, CDCl$_3$): δ 9.52 (s, 2H), 8.05 (d, $^3J_{HH}$=6.9 Hz, 2H), 7.36-7.21 (m, 6H), 3.16 (m, 2H), 1.32 (d, $^3J_{HH}$=6.6. Hz, 12H), 0.98 (d, $^3J_{HH}$=6.9 Hz, 12H).

General procedure for the preparation of N,N'-Diarylethylenediamine hydrochloride 3. Borane-tetrahydrofuran complex (1M solution in THF, 125 mL, 6.25 equiv) was added dropwise with stirring to oxamide (20 mmol) at r.t. The reaction mixture was refluxed overnight, allowed to cool to r.t. and excess borane was quenched by careful, dropwise addition of water until no more gas evolution was observed. The reaction mixture was concentrated in vacuo, extracted with ether and the organic extracts were dried over Na$_2$SO$_4$. 2M HCl in ether (30 mL, 3 equiv) was then added to the dry organic extracts and the resulting white precipitate was collected by filtration, washed with a small amount of ethanol and dried in vacuo. The following N,N'-diarylethylenediamine hydrochlorides were prepared by this procedure:

N,N'-Bis(o-tolyl)ethylenediamine hydrochloride 3a (i.e. compound 3 wherein R=methyl). Obtained in a 89% yield as a white solid. $^1$H NMR (300 MHz, D$_2$O): δ 7.30-7.10 (m, 8H), 3.67 (s, 4H), 2.45 (s, 6H).

N,N'-Bis(2-ethylphenyl)ethylenediamine hydrochloride 3b (i.e. compound 3 wherein R=ethyl). Obtained in a 74% yield as a white solid.

N,N'-Bis(2-isopropylphenyl)ethylenediamine hydrochloride 3c (i.e. compound 3 wherein R=isopropyl). Obtained in a 91% yield as a white solid. $^1$H NMR (300 MHz, D$_2$O): δ 7.33 (d, $^3J_{HH}$=6.9 Hz, 2H), 7.15 (m, 4H), 6.98 (d, $^3J_{HH}$=6.9 Hz, 2H), 3.51 (s, 4H), 2.74 (m, 2H), 0.98 (d, $^3J_{HH}$=6.9 Hz, 12H).

General procedure for the preparation of NHC ligand precursor 4 or Dihydroimidazolium salt 4. Triethyl orthoformate (150 mL) was added to the diamine hydrochloride 3 in a 250-mL r.b. flask. The flask was equipped with a distillation head and heated for about 1 h, during which ethanol distilled over at 78-80° C., followed by about 70 mL of triethyl orthoformate at 135-140° C. The reaction mixture was then allowed to cool to r.t., diluted with hexanes and the white precipitate was collected by filtration, washed with hexanes and ether and dried in vacuo. The following dihydroimidazolium salts were prepared by this procedure:

1,3-Bis(o-tolyl)-4,5-dihydroimidazolium chloride 4a (i.e. compound 4 wherein R=methyl). Obtained in a 93% yield as a white solid. $^1$H NMR (300 MHz, CDCl$_3$): δ 8.83 (s, 1H), 7.78-7.21 (d, 8H), 4.64 (s, 4H), 2.43 (s, 6H).

1,3-Bis(2-ethylphenyl)-4,5-dihydroimidazolium chloride 4b (i.e. compound 4 wherein R=ethyl). Obtained in a 74% yield as a white solid. $^1$H NMR (300 MHz, CD$_2$Cl$_2$) δ 9.04 (1H, s), 7.92 (2H, d, J=7.5 Hz), 7.47-7.30 (6H, m), 4.64 (4H, s), 2.78 (4H, q, J=7.8 Hz), 1.31 (6H, t, J=7.8 Hz).

1,3-Bis(2-isopropylphenyl)-4,5-dihydroimidazolium chloride 4c (i.e. compound 4 wherein R=isopropyl).

Obtained in an 84% yield as a white solid. $^1$H NMR (300 MHz, CDCl$_3$): δ 8.22 (d, $^3J_{HH}$=7.2 Hz, 2H), 8.04 (s, 1H), 7.34 (m, 6H), 4.73 (s, 4H), 3.06 (m, 2H), 1.29 (d, $^3J_{HH}$=6.0 Hz, 12H).

Example 2

Catalyst Synthesis

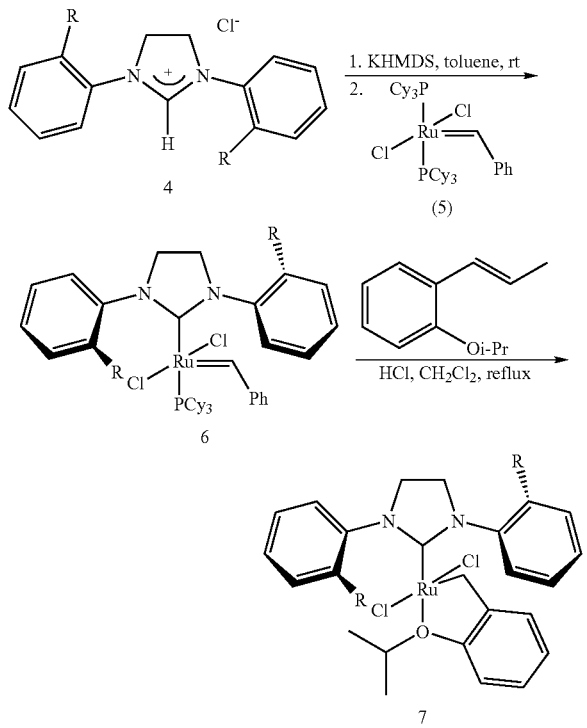

General procedure for the preparation of ortho-substituted catalyst 6. Potassium bis(trimethylsilyl)amide (1.4 g, 7.0 mmol, 1.23 equiv) was added to a suspension of dihydroimidazolium salt 4 (compound 4 of reaction scheme 3) (2.3 g, 6.7 mmol, 1.15 equiv) in toluene (57 mL) under argon. The reaction mixture was stirred at r.t. for 30 min, then compound 5 (4.7 g, 5.7 mmol) was added and stirring was continued for 1.5 h at r.t. The reaction mixture was then concentrated and catalyst 6 was isolated by column chromatography and dried in vacuo. The ortho-substituted catalysts were prepared by this procedure:

Catalyst 6a (i.e. compound 6 wherein R=methyl). Obtained in a 66% yield after column chromatography on silica gel (unreacted 5 was first eluted with 1:9 EtOAc-hexanes, then 6a was eluted with 1:3 EtOAc-hexanes). Brown crystalline solid. $^1$H NMR (300 MHz, C$_6$D$_6$): δ 19.61 (s), 8.70 (br), 7.64 (br), 7.31-6.76 (m), 6.59 (m), 6.34 (br), 3.53-3.01 (m), 2.62 (s), 2.20-2.04 (br), 1.67-1.06 (m). $^{31}$P NMR (121 MHz, C$_6$D$_6$): δ 27.87 (s), 25.15 (s).

Catalyst 6b (i.e., compound 6 wherein R=ethyl) Obtained in a 60% yield after column chromatography on silica gel (unreacted 5 was first eluted with 1:9 EtOAc-hexanes, then 6a was eluted with 1:3 EtOAc-hexanes). Brown crystalline solid. $^1$H NMR (300 MHz, C$_6$D$_6$): δ 19.59 (s), 8.74-8.62 (m), 8.25 (br), 7.71 (br), 7.34-6.85 (m), 6.67 (m), 6.44 (br), 3.55-3.07 (m), 2.79-2.19 (m), 1.69-0.91 (m), 1.67-1.06 (m). $^{31}$P NMR (121 MHz, C$_6$D$_6$): δ 25.75 (s), 25.04 (s).

Catalyst 6c (i.e. compound 6 wherein R=isopropyl). Obtained in a 68% yield after column chromatography on silica gel (unreacted 5 was first eluted with 1:10 EtOAc-hexanes, then 6c was eluted with 1:3 EtOAc-hexanes). Brown crystalline solid. $^1$H NMR (300 MHz, C$_6$D$_6$): δ 19.68 (s), 19.49 (s), 8.93-8.87 (m), 8.30 (b), 7.60 (d), 7.34-7.12 (m), 6.97 (t), 6.80 (d), 6.70-6.44 (m), 3.85-3.08 (m), 2.22-2.12 (q), 2.02-1.91 (q), 1.66-0.97 (m). $^{31}$P NMR (121 MHz, C$_6$D$_6$): δ 26.33 (s), 23.92 (s).

General procedure for the preparation of ortho-substituted Catalyst 7. 2-Isopropoxy-β-methylstyrene (0.89 g, 5.1 mmol, 2 equiv) was added to a solution of catalyst 6 (2.1 g, 2.5 mmol) in CH$_2$Cl$_2$ (25 mL). The reaction mixture was refluxed for 1 h, then 2N HCl in methanol (1.8 mL, 3.6 mmol, 1.5 equiv) was added and the mixture was refluxed for another 1 h, then evaporated to dryness in vacuo. The residue was dissolved in a minimal amount of CH$_2$Cl$_2$ and catalyst 7 was precipitated by addition of pentane. It was collected by filtration and dried in vacuo. The following ortho-substituted catalysts were prepared by this procedure:

Catalyst 7a (i.e., compound 7 wherein R=methyl). Obtained in a 71% yield after column chromatography on silica gel (eluted with 1:5 EtOAc-hexanes). Green crystalline solid. $^1$H NMR (300 MHz, CD$_2$Cl$_2$): δ 16.47 (s, 1H), 8.59 (s, 1H), 7.43 (br, 8H), 6.91 (d, $^3J_{HH}$=5.1 Hz, 3H), 4.97 (m, 1H), 4.38 (s, 2H), 4.10 (s, 2H), 2.53 (s, 6H), 1.34 (br, 6H).

Catalyst 7b (i.e. compound 7 wherein R=ethyl). Obtained in a 68% yield after column chromatography on silica gel (eluted with 1:5 EtOAc-hexanes). Green crystalline solid $^1$H NMR (300 MHz, CD$_2$Cl$_2$): δ 16.48 (s, 1H), 8.56 (br, 1H), 7.53 (m, 8H), 6.89 (d, $^3J_{HH}$=6.6 Hz, 3H), 4.95 (m, 1H), 4.42 (s, 2H), 4.10 (s, 2H), 2.93 (br, 4H), 1.37 (br, 12H).

Catalyst 7c (i.e. compound 7 wherein R=isopropyl). Obtained in a 77% yield as a green crystalline solid. $^1$H NMR (300 MHz, C$_6$D$_6$): δ 16.65 (s), 16.46 (s), 9.18 (m), 7.90 (d), 7.40-6.93 (m), 6.59 (t), 6.34 (d, $^3J_{HH}$=7.5 Hz), 4.47 (m), 3.80-3.32 (m), 2.66 (br), 1.95-1.12 (m).

Example 3

Catalyst Performance in RCM

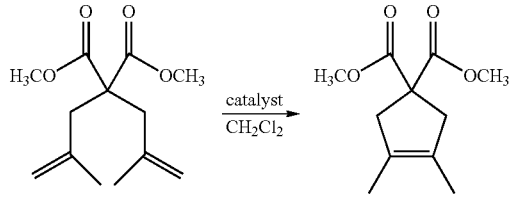

Ring-closing metathesis of dimethyl 2,2-di(2-methylallyl) malonate. Catalyst was added to a 0.1 M solution of dimethyl 2,2-di(2-methylallyl)malonate in CH$_2$Cl$_2$ in a round bottom (r.b.) flask. The flask was equipped with a reflux condenser and a bubbler outlet. The reaction mixture was sparged with argon for 5 min, then heated to desired temperature. Reaction progress was monitored by GC analysis of aliquots after removing the catalyst by treating the aliquot with 1M solution of THMP in IPA, heating the quenched mixture at 60° C. for 1 h, diluting it with water and extraction with EtOAc. The activity of catalysts of the invention were compared with the olefin metathesis catalyst (A) shown below:

TABLE 3

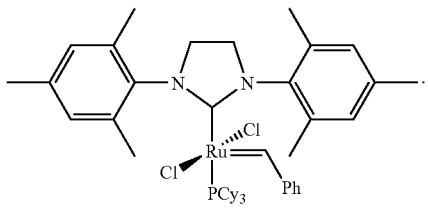

A

RCM of dimethyl 2,2-di(2-methylallyl) malonate
with 5 mol % of A at 40° C.

| Time (min) | Starting Material (GC %) | Product (GC %) |
|---|---|---|
| 30 | 91.9 | 3.0 |
| 60 | 92.4 | 4.2 |
| 180 | 84.3 | 15.7 |
| 1080 | 49.7 | 44.7 |
| 1440 | 42.4 | 49.8 |
| 2520 | 38.1 | 54.5 |

TABLE 4

RCM of dimethyl 2,2-di(2-methylallyl)malonate
with 5 mol % of 6a at 40° C.

| Time (min) | Starting Material (GC %) | Product (GC %) |
|---|---|---|
| 15 | 16.2 | 80.9 |
| 30 | 12.1 | 83.7 |
| 45 | 11.2 | 85.4 |
| 60 | 11.1 | 86.4 |
| 90 | 11.0 | 87.5 |
| 120 | 10.9 | 86.7 |
| 240 | 10.9 | 86.8 |

TABLE 5

RCM of dimethyl 2,2-di(2-methylallyl)malonate
with 5 mol % of 6b at 40° C.

| Time (min) | Starting Material (GC %) | Product (GC %) |
|---|---|---|
| 15 | 34.0 | 61.5 |
| 30 | 30.1 | 69.9 |
| 45 | 28.7 | 70.7 |
| 60 | 28.0 | 70.9 |
| 120 | 27.1 | 70.6 |
| 240 | 27.7 | 72.3 |
| 480 | 27.2 | 72.8 |

TABLE 6

RCM of dimethyl 2,2-di(2-methylallyl)malonate
with 5 mol % of 6c at 40° C.

| Time (min) | Starting Material (GC %) | Product (GC %) |
|---|---|---|
| 15 | 25.2 | 71.5 |
| 30 | 23.0 | 73.0 |
| 45 | 22.1 | 73.1 |
| 60 | 21.9 | 74.3 |
| 90 | 21.2 | 75.0 |
| 120 | 20.8 | 75.5 |
| 240 | 19.2 | 75.1 |

TABLE 7

RCM of dimethyl 2,2-di(2-methylallyl)malonate
with 5 mol % of 6c at 30° C.

| Time (min) | Starting Material (GC %) | Product (GC %) |
|---|---|---|
| 15 | 37.9 | 54.0 |
| 30 | 27.9 | 65.5 |
| 45 | 25.7 | 67.2 |
| 60 | 25.8 | 69.8 |
| 240 | 22.7 | 69.8 |
| 1140 | 20.7 | 69.5 |

TABLE 8

RCM of dimethyl 2,2-di(2-methylallyl)malonate
with 1 mol % of 6c at 30° C.

| Time (min) | Starting Material (GC %) | Product (GC %) |
|---|---|---|
| 15 | 50.9 | 46.3 |
| 30 | 47.6 | 49.4 |
| 45 | 46.6 | 51.0 |
| 60 | 45.5 | 51.6 |
| 90 | 44.2 | 52.8 |
| 120 | 44.0 | 53.7 |
| 360 | 41.2 | 54.9 |

TABLE 9

RCM of dimethyl 2,2-di(2-methylallyl)malonate
with 5 mol % of 7a at 40° C.

| Time (h) | Starting Material (GC %) | Product (GC %) |
|---|---|---|
| 0.5 | 65.8 | 30.6 |
| 1 | 52.3 | 44.7 |
| 3 | 31.5 | 65.1 |
| 18 | 28.4 | 69.9 |
| 24 | 28.3 | 70.0 |
| 42 | 27.5 | 68.8 |

TABLE 10

RCM of dimethyl 2,2-di(2-methylallyl)malonate
with 5 mol % of 7b at 40° C.

| Time (h) | Starting material (GC %) | Product (GC %) |
|---|---|---|
| 0.25 | 96.7 | 0.7 |
| 0.50 | 89.3 | 3.3 |
| 0.75 | 81.8 | 11.8 |
| 1 | 71.1 | 21.5 |
| 2 | 57.7 | 34.7 |
| 4 | 51.4 | 42.9 |
| 8 | 38.9 | 55.9 |
| 24 | 36.4 | 58.6 |

TABLE 11

RCM of dimethyl 2,2-di(2-methylallyl)malonate
with 5 mol % of 7c at 40° C.

| Time (h) | Starting Material (GC %) | Product (GC %) |
|---|---|---|
| 0.25 | 97.2 | 0.7 |
| 0.50 | 93.8 | 2.9 |

TABLE 11-continued

RCM of dimethyl 2,2-di(2-methylallyl)malonate
with 5 mol % of 7c at 40° C.

| Time (h) | Starting Material (GC %) | Product (GC %) |
|---|---|---|
| 0.75 | 87.2 | 9.3 |
| 1 | 81.7 | 15.6 |
| 1.5 | 71.9 | 24.2 |
| 2 | 69.7 | 27.5 |
| 6 | 63.4 | 32.0 |
| 24 | 63.4 | 32.5 |

Figure 2:
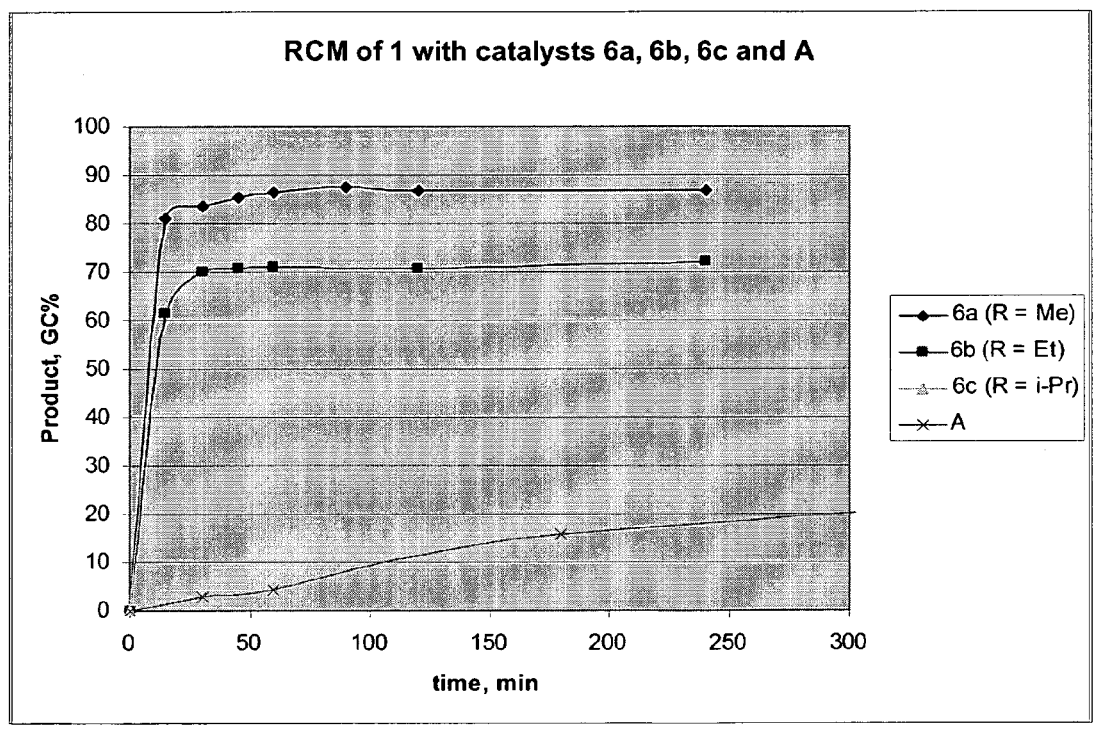
FIG. 2 shows a diagram illustrating the results of a ring-closing metathesis of 1 with catalysts 6a, 6b, 6c and A (referred to as C848 in graph), reported in Example 3 and in particular in Tables 3 to 6.
Figure 3:
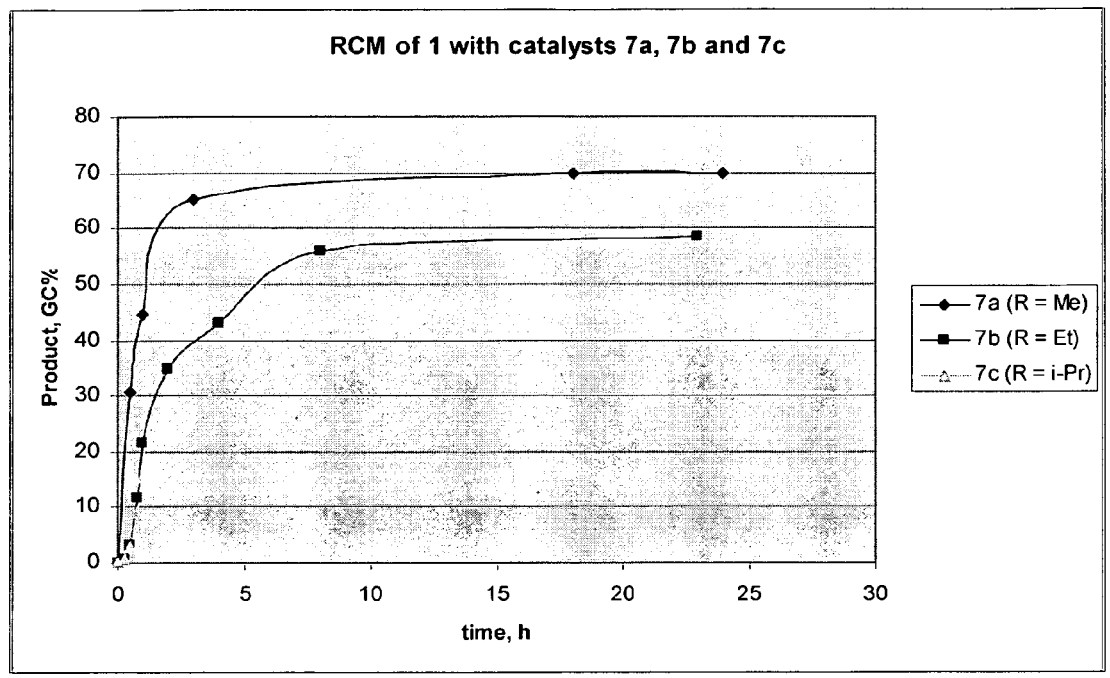
FIG. 3 shows a diagram illustrating the results of a ring-closing metathesis of 1 with catalysts 7a, 7b, 7c, reported in Example 3 and in particular in Tables 9 to 11.

The results of the RCM performed with second generation catalysts and second generation catalysts with chelating carbene ligands reported above are further illustrated in the charts shown in FIG. 2 and FIG. 3. FIG. 2 shows that catalysts 6a, 6b and 6c perform much better than catalyst A in the RCM of compound 1. Indeed, the reactions catalyzed by 6a, 6b and 6c reach much higher conversions (between about 70% and about 90% conversion) compared to the reactions catalyzed by A (about 20% conversion). Additionally, the data represented on FIG. 2 demonstrate that catalysts 6a, 6b and 6c require short reaction times and mild temperatures to reach high conversions. For example, catalyst 6a gives a high conversion (i.e., greater than 80%) within only 15 minutes at 40° C., compared to 7 hours at 60° C. for catalyst 12. FIG. 3 shows that catalysts 7a, 7b and 7c are also more active than A in the RCM of compound 1, but are less active than catalysts 6a, 6b and 6c.

Example 4

Cross Metathesis Studies

Catalyst performance in cross-metatheses involving hindered olefins Inside the glovebox, a 4-mL vials was charged with approximately 1 mL of the appropriate hindered olefin solution (2M in $CH_2Cl_2$) followed by one equivalent of 5-hexene. The appropriate amount of the tested catalyst was added to the vial; after which it was sealed and heated to desired temperature. Reaction progress was monitored by GC analysis of aliquots after removing the catalyst by treating the aliquot with 1M solution of THMP in IPA, heating the quenched mixture at 60° C. for 1 h, diluting it with water and extraction with EtOAc. An identical cross-metathesis reaction was run with A for comparison.

Cross metathesis (CM) of 5-decene ($5C_{10}$) and 2,5-dimethyl-3-hexene using 1 mol % of 6a and A at 40° C.

TABLE 12

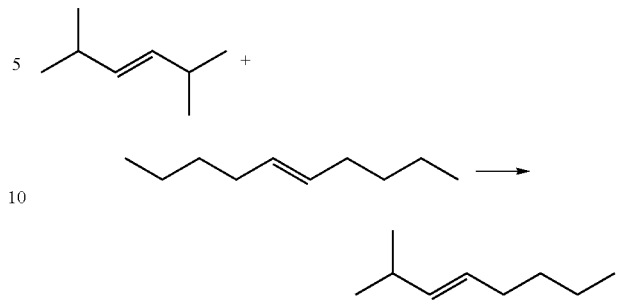

Results of CM of $5C_{10}$ and 2,5-dimethyl-3-hexene using 1 mol %
of 6a and A at 40° C.

| | Product (GC %) | | |
|---|---|---|---|
| | 0.5 h | 1 h | 40 h |
| 6a | 20.0 | 23.9 | 29.9 |
| A | 11.8 | 15.3 | 7.8 |

Cross metathesis of 5-decene, $5C_{10}$, and 2-methyl-1-nonene using 1 mol % of 6b, 6c, 6a and A at 40° C.

TABLE 13

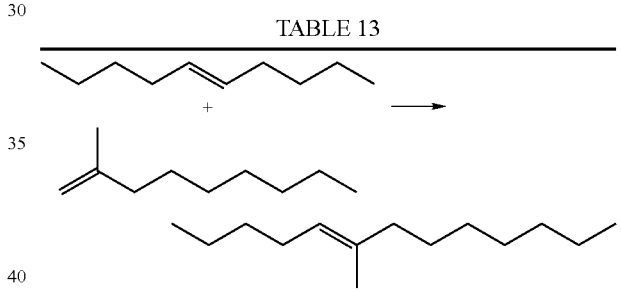

Results of CM of $5C_{10}$ and 2-methyl-1-nonene
using 1 mol % of 6b, 6c, 6a and A at 40° C.

| | Product (GC %) | | |
|---|---|---|---|
| | 1 h | 3 h | 6 h |
| 6b | 27.4 | 28.4 | 29.0 |
| 6c | 22.2 | 23.5 | 24.0 |
| 6a | 20.1 | 19.5 | 20.0 |
| A | 15.2 | 21.7 | 25.6 |

Example 5

Catalyst performance in self-metathesis of methyl oleate Inside the glovebox, a 4-mL vial was charged with approximately 10 g of methyl oleate. The appropriate amount of a stock solution of 6a in benzene was added to the vial, after which it was sealed and heated to 40° C. Reaction progress was monitored by GC analysis of aliquots after removing the catalyst by treating the aliquot with 1M solution of THMP in IPA, heating the quenched mixture at 60° C. for 1 h, diluting it with water and extraction with EtOAc.

Self metathesis (SM) of neat methyl oleate using 2, 5 and 20 ppm of 6a and A at 40° C.

TABLE 14

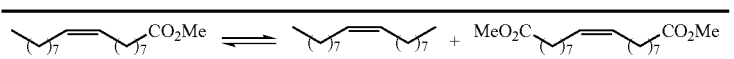

results of SM of neat methyl oleate using 2, 5 and 20 ppm of 6a and A at 40° C.

| | Maximum conversion[a] reached at, min | | |
|---|---|---|---|
| | 2 ppm | 5 ppm | 20 ppm |
| 6a | 30 | 10 | 5 |
| A | 30 | 10 | <10 |

[a]Maximum conversion in this reaction corresponds to a mixture containing 50 mol % of the starting material and 25 mol % of each of the products (25 mol % 9-octadecene and 25 mol % 1,18-dimethyl-octadecenoate)

Example 6

Preparation of Salt 10

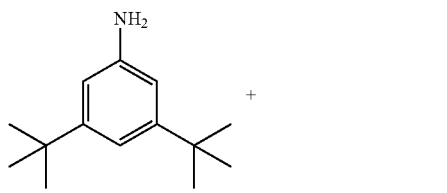

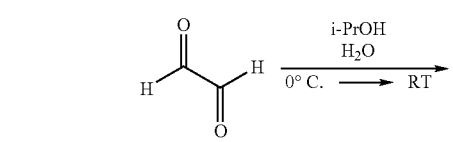

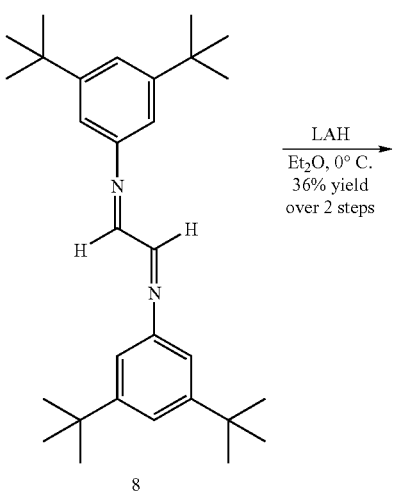

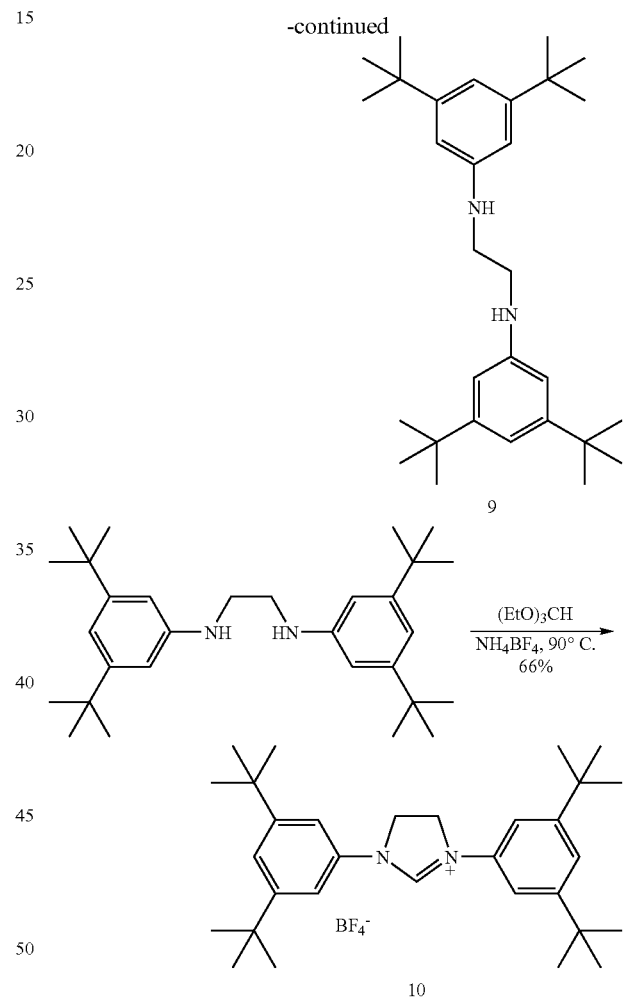

Preparation of Dianine 9. This is a two step procedure. In the first step, a 40% solution of glyoxal in water (465 µl, 4.1 mmol) was added to 3,5-di-tert-butylaniline (1.83 g, 8.9 mmol) in isopropanol (16 ml) and water (16 ml) at 0° C. The reaction stirred for 7 hours and during this time it warmed to room temperature. The reaction mixture was filtered through a glass frit; the filtrate was dissolved in $CH_2Cl_2$, dried over $MgSO_4$, filtered through another glass flit and concentrated. This crude reaction product was then dissolved in $Et_2O$ (50 ml) and added to LAH (570 mg, 15 mmol) in $Et_2O$ (50 ml) at 0° C. The reaction stirred for 36 hours and warmed to room temperature. The reaction was quenched with $H_2O$ (570 µl), 15% $NaOH/H_2O$ (570 µl), $H_2O$ (2 ml), filtered through a glass frit dried over $MgSO_4$, filtered through another glass frit and concentrated. The reaction mixture was then purified by flash column chromatography (30% EtOAc/Hexanes) to yield 9 (786 mg, 36% over two steps) as an oil. $^1$H NMR (300 MHz, CDCl$_3$) δ 6.85 (2H, t, J=1.5 Hz), 6.55 (4H, d, J=1.8 Hz), 5.31 (2H, s), 3.45 (4H, s), 1.31 (36H, s); $^{13}$C (75 MHz, CDCl$_3$) δ 152.1, 147.8, 112.8, 107.9, 44.1, 35.1, 31.7; HRMS (EI+) calc for C$_{30}$H$_{49}$N$_2$, 437.3896. Found 437.3902.

Preparation of NHC ligand precursor 10. To diamine 9 (786 mg, 1.8 mmol), was added (EtO)$_3$CH (3 ml, 18 mmol), NH$_4$BF$_4$ (189 mg, 1.8 mmol) and formic acid (2 drops). The reactions stirred at 90° C. for 48 hours. Et$_2$O was added to precipitate the salt. The reaction mixture was then filtered and the solids were washed with Et$_2$O and collected to yield 8 (633 mg, 66%) as a white solid. $^1$H NMR (300 MHz, CDCl$_3$) δ 8.57 (1H, s), 7.42 (2H, t, J=1.5 Hz), 7.23 (4H, d, J=1.8 Hz), 4.69 (4H, s), 1.32 (36H, s); $^{13}$C (75 MHz, CDCl$_3$) δ 153.6, 151.4, 135.4, 123.1, 114.9, 50.5, 35.4, 31.5.

Alternate preparation of diamine 9:

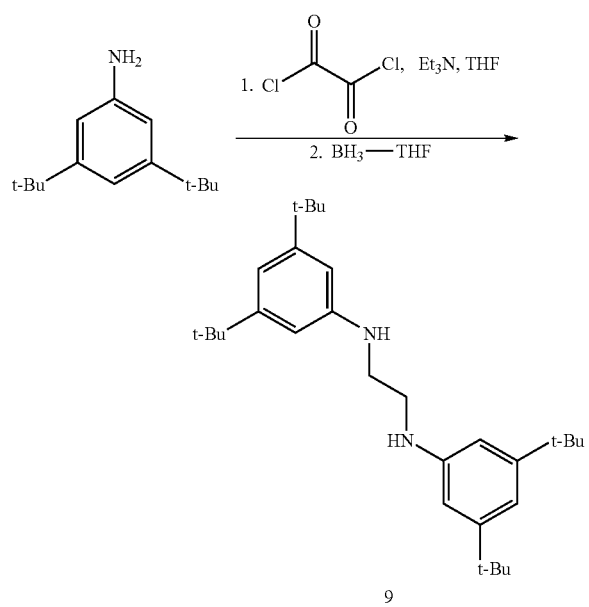

N,N'-Bis(3,5-di-t-butylphenyl)oxamide. Oxalyl chloride (2.16 mL, 25 mmol) was added dropwise to a stirred solution of 3,5-di-t-butylaniline (10.28 g, 50 mmol) and triethylamine (7.0 mL, 50 mmol) in THF (200 mL) at 0° C. Upon addition, the reaction was allowed to warm up to r.t. and stirred for 1 h. The reaction mixture was then concentrated in vacuo and diluted with water (100 mL). The white precipitate was collected by filtration, washed with dilute HCl (100 mL), water (2×100 mL), and dried in vacuo. Obtained 9.07 g (78%) of N,N'-Bis(3,5-di-t-butylphenyl)oxamide as a white solid.

N,N'-Bis(3,5-di-t-butylphenyl)ethylenediamine (9). A 1M solution of BH$_3$-THF in THF (125 mL, 125 mmol) was added dropwise with stirring to the solid oxamide (9.06 g, 19.52 mmol) at r.t. The resulting homogeneous mixture was then refluxed for 15 h, allowed to cool down to r.t. and carefully quenched by adding water. The mixture was then concentrated and extracted with ether. Column chromatography (2:1 hexanes—dichloromethane, silica gel) afforded 6.51 g (76%) of pure 9 as a colorless oil and 1.27 g of impure 9 (contaminated with 3,5-di-t-butylaniline) which was subjected to a second chromatographic purification. The combined yield of 9 was 86%. $^1$H NMR (300 MHz, CDCl$_3$) δ 6.85 (2H, t, J=1.5 Hz), 6.55 (4H, d, J=1.8 Hz), 5.31 (2H, s), 3.45 (4H, s), 1.31 (36H, s); $^{13}$C (75 MHz, CDCl$_3$) δ 152.1, 147.8, 112.8, 107.9, 44.1, 35.1, 31.7; HRMS (EI+) calc for C$_{30}$H$_{49}$N$_2$, 437.3896. Found 437.3902.

Example 7

Preparation of Catalyst 12

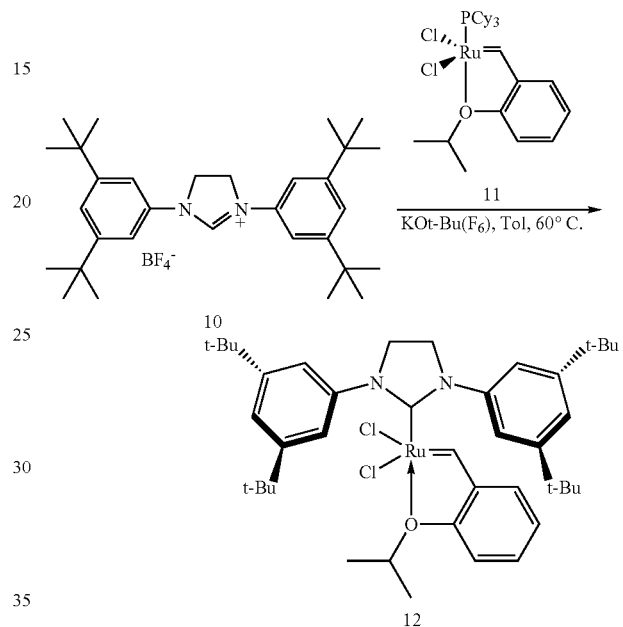

Figure 4:
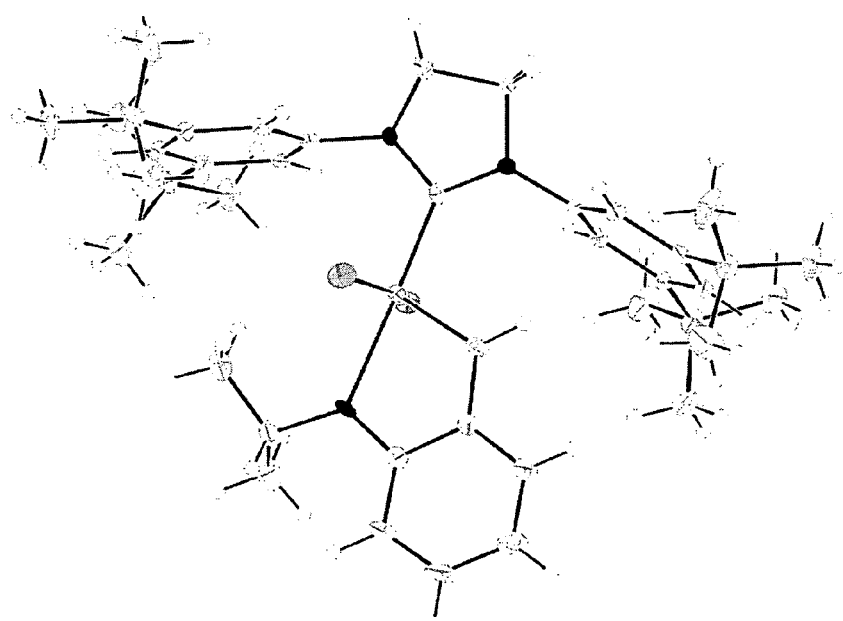
FIG. 4 depicts the single crystal X-ray structure was obtained for catalyst 12 described in Example 7.

Preparation of Catalyst 12. NHC ligand precursor 10 (156 mg, 0.3 mmol), KOt-Bu(F$_6$) (66 mg, 0.3 mmol), and ruthenium complex 11 (132 mg, 0.22 mmol) were all combined in toluene in a glove box. The flask was removed and stirred at 60° C. for 18 hours in a fume hood. The reaction mixture was then directly purified by flash column chromatography (5% Et$_2$O/Hexanes, run 2 times) to yield catalyst 12 (34 mg, 20%) as a green oil. The catalyst was then lyophilized from benzene to give a pale green solid. It should be noted that by $^1$H NMR the conversion to 12 is 50%. $^1$H NMR (300 MHz, CDCl$_3$) δ 16.91 (1H, s), 8.14-8.13 (2H, m), 7.73 (2H, m), 7.64 (1H, m), 7.52 (1H, m), 7.06-6.92 (2H, m), 6.62 (1H, t, J=7.5 Hz), 6.31 (1H, d, J=8.4 Hz), 4.47 (1H, quint, J=6 Hz), 3.51 (4H, s), 1.51 (18H, s), 1.35 (6H, d, J=6 Hz), 1.24 (18H, s); HRMS (EI+) calc for C$_{41}$H$_{58}$N$_2$OCl$_2$Ru 766.2970. Found 766.3007. FIG. 4 depicts the single crystal X-ray structure was obtained for catalyst 12.

Example 8

Catalyst Activity Studies

Preparation of stock solutions. Catalyst 12 (14 mg) was placed in a 2 ml volumetric flask and taken into a glove box. In the glove box, 2 ml of CD$_2$Cl$_2$ was added to make stock solution Z. 0.44 ml of Z was then transferred to another 2 ml volumetric flask and diluted to 2 ml with CD$_2$Cl$_2$ to make stock solution Y.

Reaction Scheme 10.

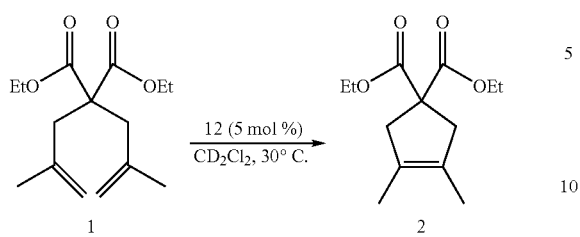

Figure 5:
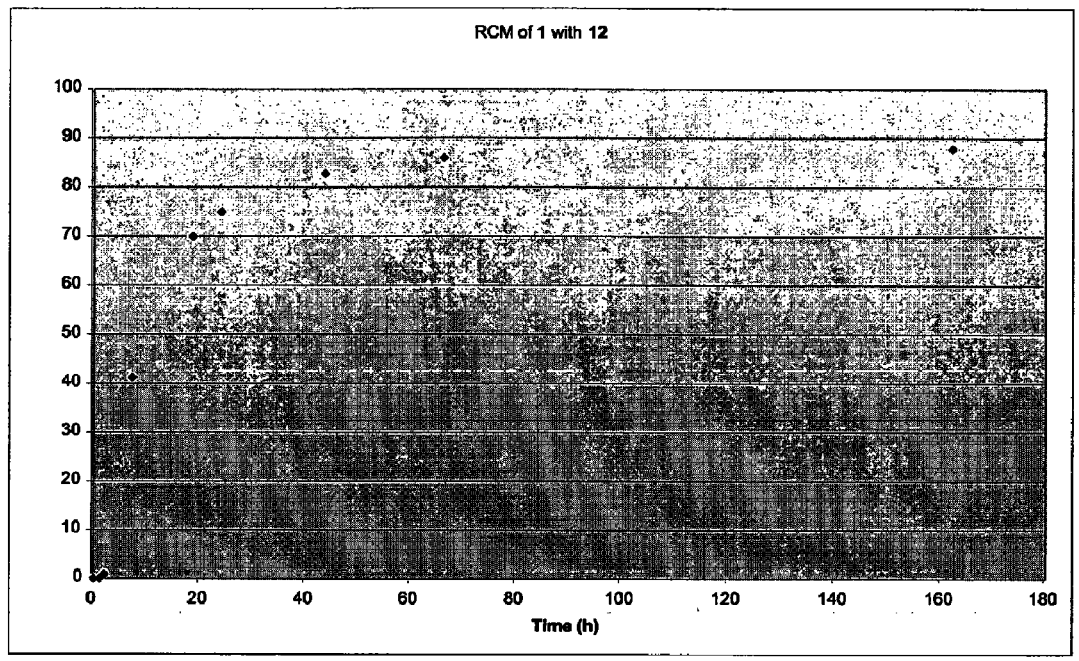
FIG. 5 is a graph of the conversion over time for the ring-closing metathesis of 1 with catalyst 12, described in Example 8.

In a glove box, 0.44 ml of stock solution Z (3.1 mg of 12, 0.004 mmol) was transferred to a screw cap NMR tube. CD$_2$Cl$_2$ (0.36 ml) was added and then 1 (21.5 μl, 0.08 mmol). The NMR tube was sealed, removed from the glove box and heated to 30° C. FIG. 5 is a graph of the conversion over time, demonstrating the dramatically improved reactivity 12 shows for ring-closing metathesis (RCM) to form tetrasubstituted olefins.

Figure 6:
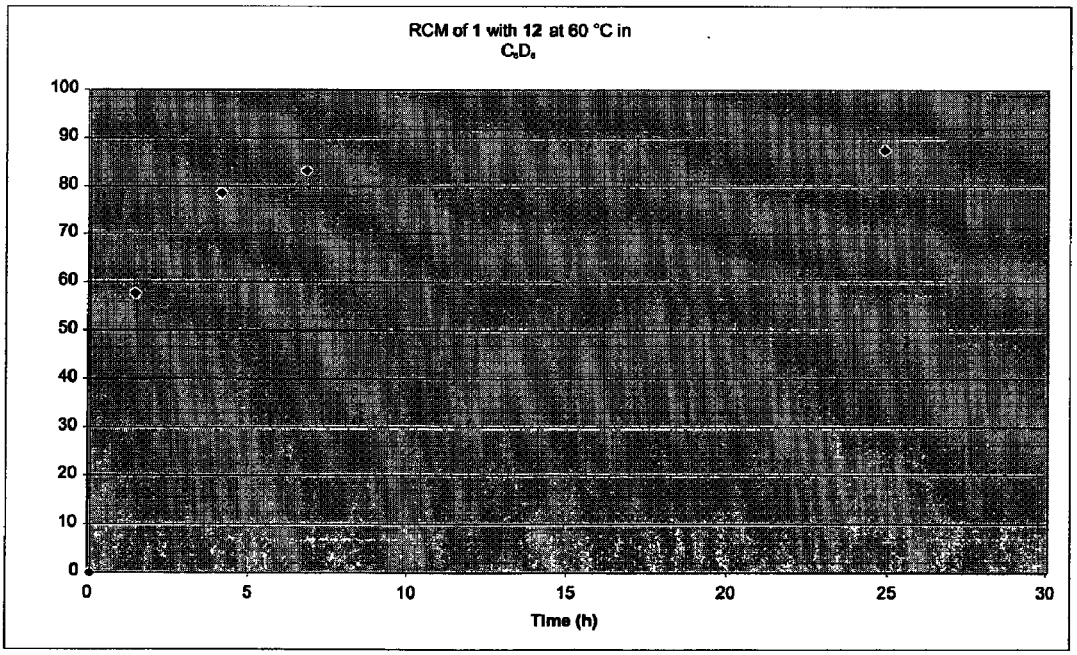
FIG. 6 is a graph of the conversion over time for the ring-closing metathesis of 1 with catalyst 12 in $C_6D_6$, described in Example 8.

This study was repeated in C$_6$D$_6$ at 60° C. to examine the impact of temperature. Catalyst 12 (3.1 mg, 0.004 mmol) and C$_6$D$_6$ (0.8 ml) were combined in a screw cap NMR tube and 1 (21.5 μl, 0.08 mmol) was added. The NMR tube was sealed, removed from the glove box and heated to 60° C. A graph of conversion over time is shown in FIG. 6. As can be seen, after 24 hours 88% conversion has been achieved, and 83% conversion is achieved in only 7 hours.

Example 9

RCM Studies with Less Hindered Olefins

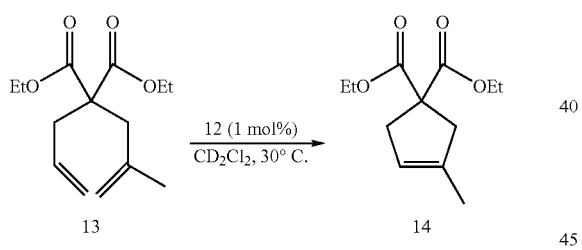

Figure 7:
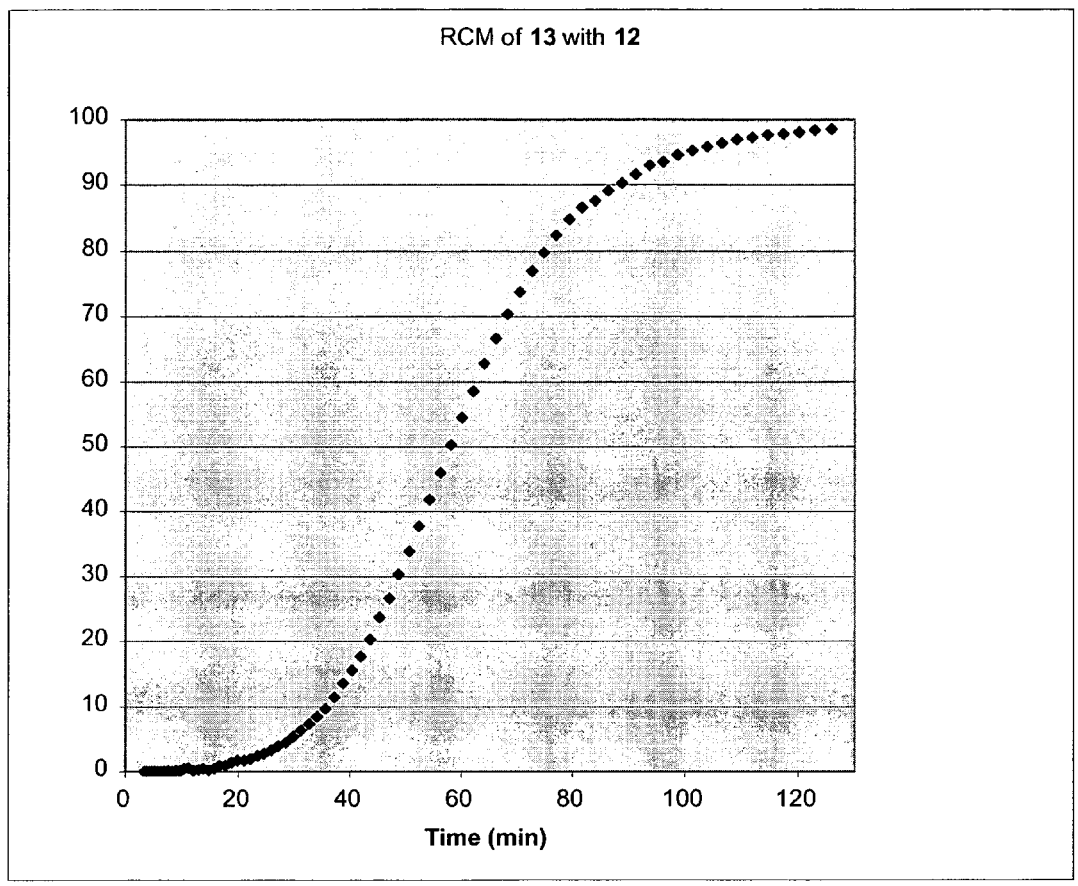
FIG. 7 is a graph of the conversion over time for the ring-closing metathesis of 13 with catalyst 12 described in Example 9.

In a glove box, 0.4 ml of stock solution Y (0.6 mg of 12, 0.0008 mmol) was transferred to a screw cap NMR tube. CD$_2$Cl$_2$ (0.4 ml) was added and the NMR tube was sealed and transferred to a 500 MHz NMR which was warmed to 30° C. The NMR tube was then ejected, 13 (20.5 μl, 0.08 mmol) was added and the tube was injected for data collection. A graph of conversion over time is shown in FIG. 7.

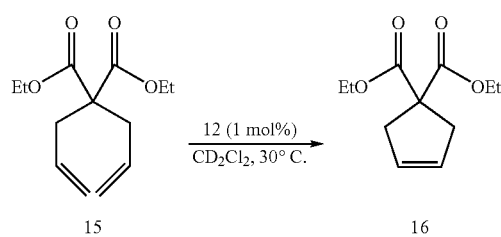

Figure 8:
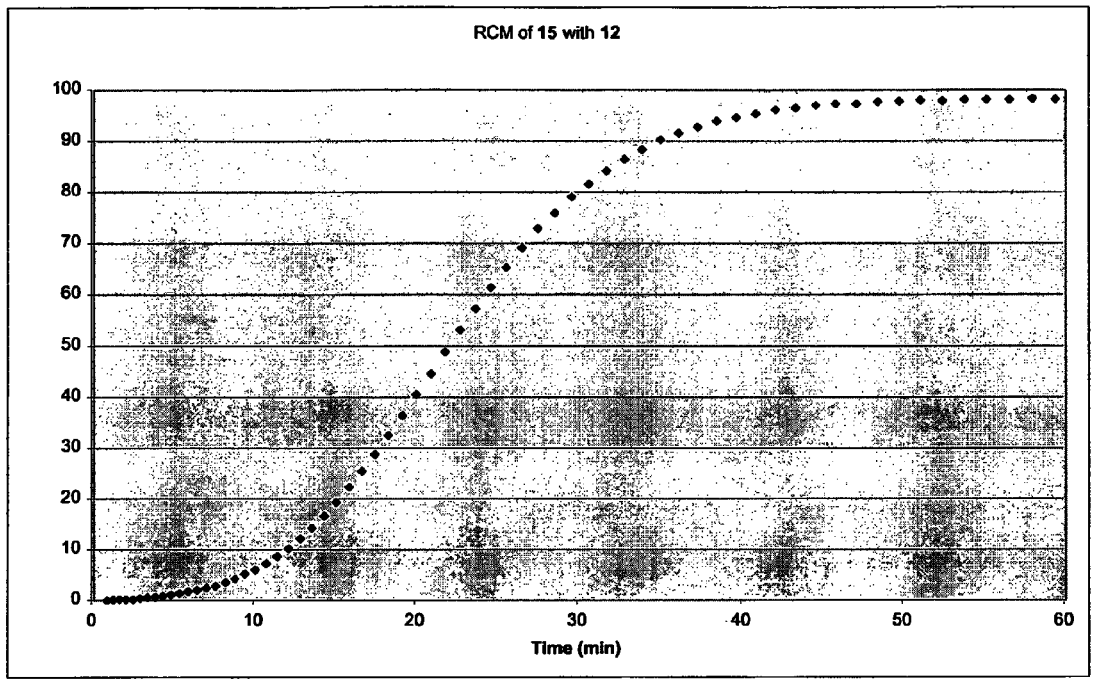
FIG. 8 is a graph of the conversion over time for the ring-closing metathesis of 15 with catalyst 12 described in Example 9.

In a glove box, 0.4 ml of stock solution Y (0.6 mg of 12, 0.0008 mmol) was transferred to a screw cap NMR tube. CD$_2$Cl$_2$ (0.4 ml) was added and the NMR tube was sealed and transferred to a 500 MHz NMR which was warmed to 30° C. The NMR tube was then ejected, 15 (19.5 μl, 0.08 mmol) was added and the tube was injected for data collection. FIG. 8 shows a graph of the conversion over time.

Example 10

Stability Studies

A striking feature of catalyst 12 is its stability. In solution (CH$_2$Cl$_2$ or Benzene), in the absence of substrate, it is stable for at least 4 weeks. As a solid, 12 is stable in air for at least 5 weeks. Finally, during the catalytic reactions described above, for the reactions performed at 30° C. the only time point the original catalyst was not observed by $^1$H NMR was 162 hours. For the reaction performed at 60° C., none of the original catalyst was observed by $^1$H NMR at 24.8 hours. Overall, catalyst 12 is highly stable.

Example 11

Preparation of Catalyst-18

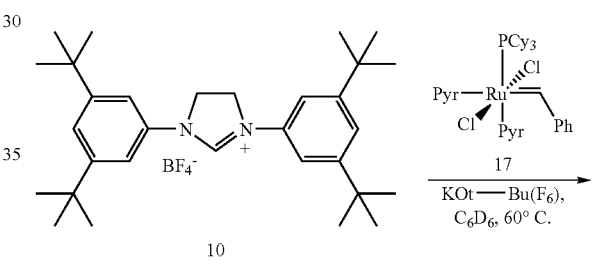

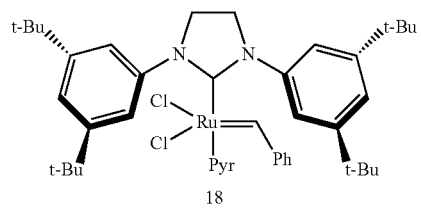

Catalyst-18. NHC ligand precursor 10 (14 mg, 0.03 mmol), KOt-Bu(F$_6$) (6 mg, 0.03 mmol), and ruthenium complex 17 (14 mg, 0.02 mmol) were all combined in C$_6$D$_6$ in a screw cap NMR tube in a glove box. The NMR tube was removed and heated at 60° C. for 1 hour in a fume hood. Conversion to catalyst 18 was determined to be 52% by proton NMR. $^1$H NMR (300 MHz, CDCl$_3$) δ 19.43 (1H, s).

It should be noted that complex 18 is relatively unstable. The phosphine analogue in which the pyridine ligand is replaced by PCy$_3$ is also unstable. It is believed that the tert-butyl groups on the NHC are so large that they actively dissosciate the pyridine and phosphine respectively. The transient stability makes these complexes less suitable for catalysis.

Example 12

Preparation of an NHC with Smaller Bis-Meta Substitution

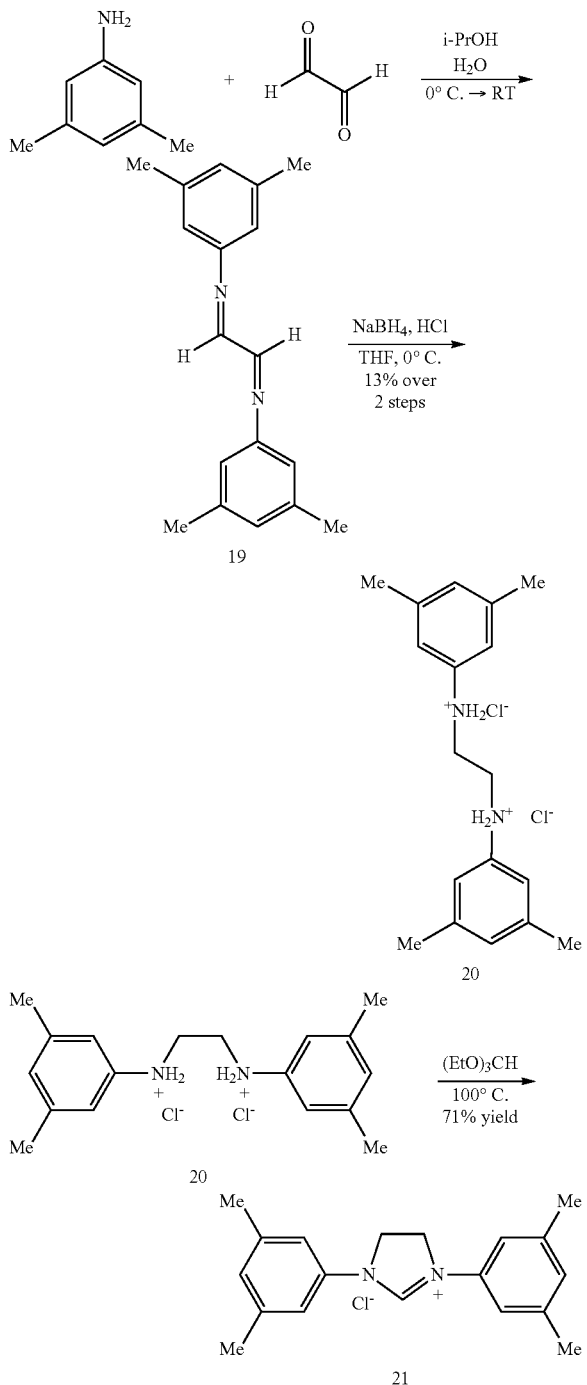

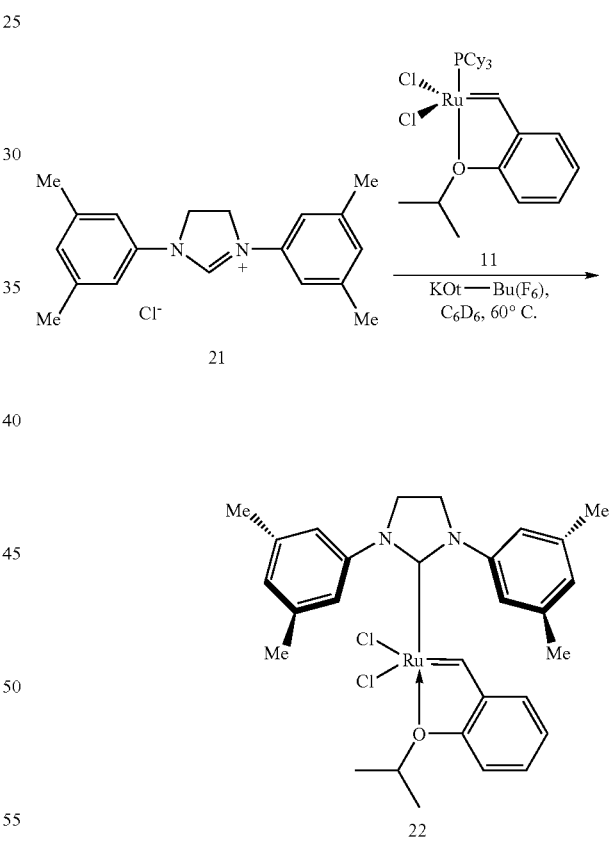

propanol (40 ml) and water (40 ml) at 0° C. The reaction stirred for 7 hours and during this time it warmed to room temperature. The reaction mixture was filtered through a glass frit; the filtrate was dissolved in $CH_2Cl_2$, dried over $MgSO_4$, filtered through another glass frit and concentrated. This crude reaction product was then dissolved in THF (37 ml) and to this at 0° C. was added $NaBH_4$ (1.5 g, 40 mmol). Concentrated HCl (1.6 ml) was added dropwise over 25 min. The reaction was stirred for 1 hour and then 4N HCl (75 ml) was added. The reaction was stirred for 1 hour and then filtered. The filtrate was wash extensively with $Et_2O$ to give diamine salt 20 (438 mg, 13% over 2 steps) as an off white solid. $^1$H NMR (300 MHz, $CDCl_3$) δ 6.84 (4H, s), 6.76 (2H, s), 3.62 (4H, s), 2.25 (12H, s).

NHC ligand precursor 21. $HC(OEt)_3$ (10 ml) was added to diamine salt 20 and the reaction was stirred at 90° C. for 14 hours. The reaction mixture was filtered and washed with $Et_2O$ to give NHC ligand precursor 21 (290 mg, 71%) as an off white solid. $^1$H NMR (300 MHz, $DMSO(D_6)$) δ 9.89 (1H, s), 7.29 (4H, s), 7.02 (2H, s), 4.54 (4H, s), 2.51-2.49 (12H, m). HRMS (EI+) calc for $C_{19}H_{23}N_2$ 279.18613. Found 279.18572.

Catalyst 22. NHC ligand precursor 21 (9 mg, 0.03 mmol), $KOt-Bu(F_6)$ (6 mg, 0.03 mmol), and ruthenium complex 911 (13 mg, 0.02 mmol) were all combined in $C_6D_6$ in a screw cap NMR tube in a glove box. The NMR tube was removed and heated at 60° C. for 2.5 hour in a fume hood. Conversion to catalyst 22 was determined to be 14% by proton NMR. $^1$H NMR (300 MHz, $CDCl_3$) δ 17.19 (1H, s).

It should be noted that complex 22 is relatively unstable. It seems that the meta-methyl groups are not large enough and the complex is difficult to handle without decomposition. For this reason, this complex is unattractive for catalysis.

Example 13

Preparation of Unsaturated Meta-Substituted NHC Ligands

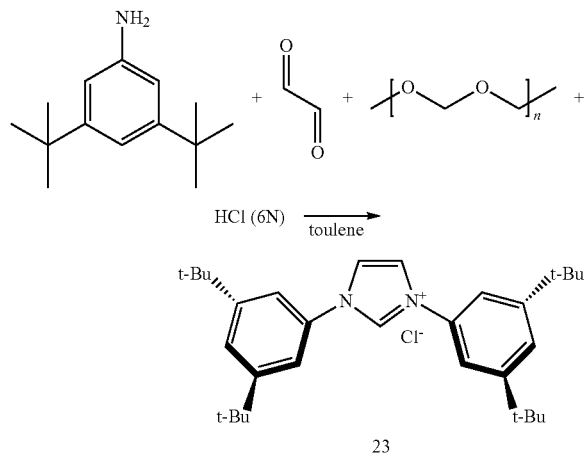

NHC ligand precursor 23. A solution of 3,5-ditertbutylaniline (3 g, 14.6 mmol) in toluene (5 ml) was added to a solution of paraformaldehyde (220 mg, 7.3 mmol) in toluene (5 ml). The reaction was then stirred at 100° C. for 1.5 hours. The reaction was cooled to 40° C. and 6N HCl (1.2 ml, 7.3 mmol) was added. The reaction was stirred for 5 minutes, glyoxal (837 μl, 7.3 mmol) was added and the reaction was stirred another 5 minutes. The reaction was stirred at 100° C. for 14 hours, cooled to RT and purified by column chromatography (5% MeOH/CH$_2$Cl$_2$) to yield a brown foam. This foam was washed with Et$_2$O to yield 806 mg (23%) of 23 as a white solid. $^1$H NMR (300 MHz, CDCl$_3$) δ 11.89 (br, 1H), 7.78-7.76 (m, 6H), 7.59 (s, 2H), 1.42 (s, 36H); $^{13}$C (75 MHz, CDCl$_3$)δ; HRMS (EI+) calc for C$_{31}$H$_{45}$N$_2$, 445.3583. Found 445.3561.

Example 14

Preparation of Catalyst 24

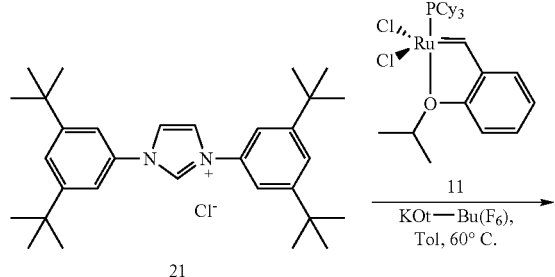

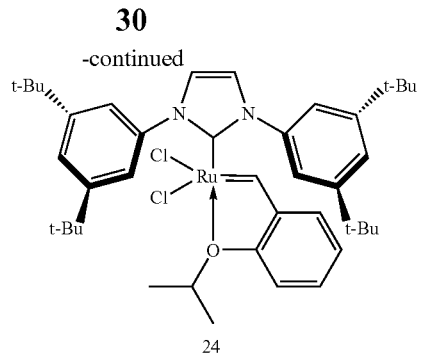

Ruthenium Catalyst 24. In a glove box, NHC ligand precursor 23 (63 mg, 0.13 mmol), ruthenium precursor 11 (78 mg, 0.13 mmol) and KOt-Bu(F$_6$) (29 mg, 0.13 mmol) were combined in toluene. The flask was sealed, removed from the glove box and stirred at 60° C. for 18 hours. The reaction was concentrated and purified by flash column chromatography (5%->20% Et$_2$O/Pent). There were 3 bands that could be isolated from this column, first 2 brown bands and then one green band. The second brown band was the desired product; however, it was not completely pure after one column. Recolumning in 10% Et$_2$O/Pentane gave a brown oil product completely pure by $^1$H NMR (9 mg, 9%) and another fraction still slightly impure (18 mg, 18%). The products were lyophilized from benzene to give solids. $^1$H NMR (300 MHz, CDCl$_3$) δ 16.78 (s, 1H), 8.13 (br, 2H), 7.74-7.62 (m, 4H), 7.07-7.04 (m, 1H), 6.97 (dd, J=3, 1.5 Hz, 1H), 6.66 (t, J=7.5 Hz, 3H), 6.34 (d, J=8.4 Hz, 1H), 4.49 (sept, J=6 Hz, 1H), 1.44 (d, J=6 Hz, 6H), 1.44 (br, 18H), 1.18 (br, 18H); $^{13}$C (75 MHz, CDCl$_3$)$_6$; HRMS (EI+) calc for C$_{41}$H$_{56}$Cl$_2$N$_2$ORu, 764.2814. Found 764.2842.

Example 15

Preparation of Catalyst 25

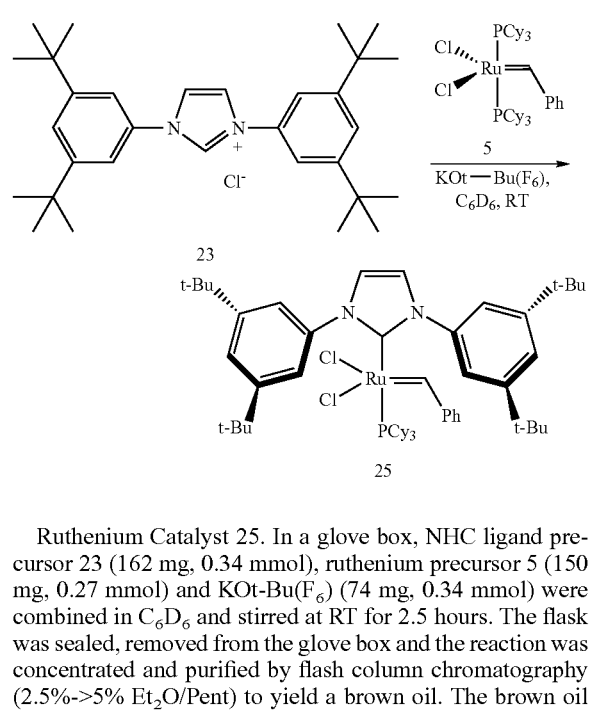

Ruthenium Catalyst 25. In a glove box, NHC ligand precursor 23 (162 mg, 0.34 mmol), ruthenium precursor 5 (150 mg, 0.27 mmol) and KOt-Bu(F$_6$) (74 mg, 0.34 mmol) were combined in C$_6$D$_6$ and stirred at RT for 2.5 hours. The flask was sealed, removed from the glove box and the reaction was concentrated and purified by flash column chromatography (2.5%->5% Et$_2$O/Pent) to yield a brown oil. The brown oil was lyophilized from benzene to give 25 as a brown solid (66 mg, 25%). $^1$H NMR (300 MHz, CDCl$_3$) δ 20.07 (d, J=10.5 Hz, 1H), 8.03 (br, 2H), 7.60 (t, 1.8 Hz, 1H), 6.86-6.81 (m, 2H), 6.51-6.47 (m, 1H), 1.81-1.07 (m).

Example 16

Preparation of Catalyst 26

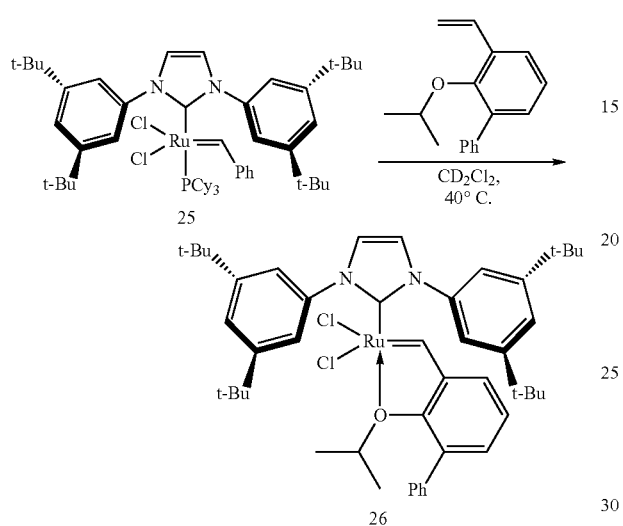

Ruthenium Catalyst 26. In a screw cap NMR tube, ruthenium compound 25 (10 mg, 0.01 mmol), 2-isopropoxy-3-vinylbiphenyl (5 mg, 0.02 mmol) and CuCl (1 mg, 0.01 mmol) were combined in CD$_2$Cl$_2$ (1 ml) in the glove box. The reaction was heated at 40° C. for 29 hours, concentrated and purified by column chromatography (10%-->25% Et$_2$O/Pentange) to yield a grayish green oil. This oil was lyophilized from benzene to yield 26 as a solid (2 mg, 25%). $^1$H NMR (300 MHz, CDCl$_3$) δ 16.77 (s, 1H), 7.89 (s, 1H), 7.66-7.59 (m, 6H), 7.50-7.38 (m, 7H), 7.02 (t, J=4.5 Hz, 1H), 6.72 (dd, J=3.6, 1.2 Hz, 1H), 4.45 (sept, J=3.6 Hz, 1H), 1.47 (s, 18H), 1.30 (s, 18H), 0.95 (d, J=3.6 Hz, 6H).

Example 17

Preparation of Para-Substituted NHC Ligand

Reaction Scheme 21

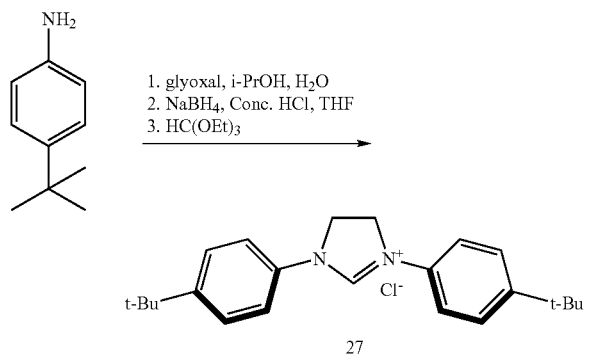

NHC ligand precursor 27. Glyoxal (1.92 ml, 16.8 mmol) was added to a solution of 4-tertbutylaniline (5.87 ml, 37 mmol), i-PrOH (60 ml) and water (60 ml). The reaction was stirred for 1 hour and then the liquids were decanted off. The remaining sticky solid was washed with i-PrOH and then any remaining solvent was removed under vacuum. THF (62 ml) was then added to the flask and it was cooled to 0° C. NaBH$_4$ (2.57 g, 68 mmol) was added to the solution. Concentrated HCl (2.7 ml) was added dropwise over 0.5 hours, and the reaction was stirred for 2 hours. 4N HCl (150 ml) was added slowly and the reaction was stirred for 0.5 hours, filtered and the filtrate was washed with Et$_2$O to give a white solid. To this filtrate was added HC(OEt)$_3$ (20 ml) and the reaction was stirred at 100° C. for 18 hours. The reaction was filtered. The filtrate was washed with Et$_2$O to give 27 as a white solid (80 mg, 1%). $^1$H NMR (300 MHz, CDCl$_3$) δ 11.35 (br, 1H), 7.89 (br, 4H), 7.38 (br, 4H), 4.44 (br, 4H), 1.15 (s, 18H); $^{13}$C (75 MHz, CDCl$_3$) δ 151.1, 150.9, 133.0, 127.3, 118.6, 48.7, 34.8, 31.3; HRMS (EI+) calc for C$_{23}$H$_{31}$N$_2$ 335.2487. Found 335.2476.

Example 18

Preparation of Catalyst 28

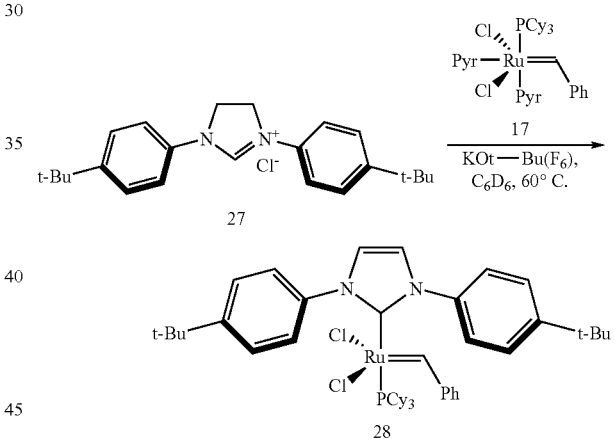

Ruthenium Compound 928 (Comparative). In a glove box, NHC ligand precursor 27 (5 mg, 0.014 mmol), ruthenium precursor 17 (10 mg, 0.014 mmol) and KOt-Bu(F$_6$) (3 mg, 0.014 mmol) were combined in C$_6$D$_6$ in a screw cap NMR tube. The tube was removed from the box and immersed in a 60° C. oil bath. The solution immediately turned brown and a new species (28) was transiently observed. $^1$H NMR (300 MHz, CDCl$_3$) δ 19.46 (d, J=6 Hz).

Example 19

Catalyst Activity

Standard activity tests were used to determined the utility of the new catalysts of the invention.

Catalyst 24.

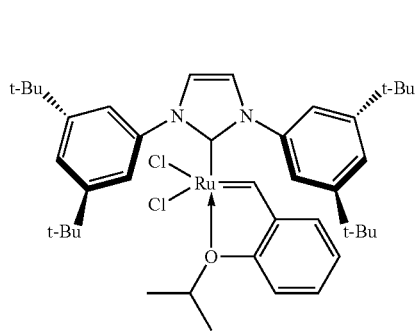

Preparation of stock solutions. Catalyst 24 (9 mg) was placed in a 2 ml volumetric flask and taken into a glove box. In the glove box, 2 ml of $CD_2Cl_2$ was added to make stock solution X. 0.33 ml of X was then transferred to another 2 ml volumetric flask and diluted to 2 ml with $CD_2Cl_2$ to make stock solution W.

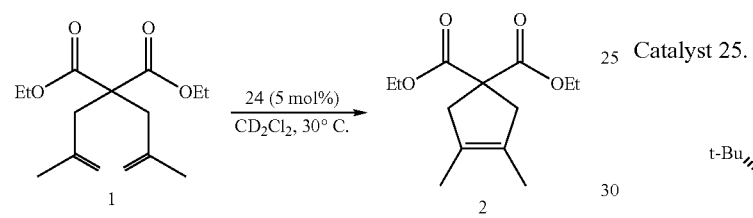

Figure 9:
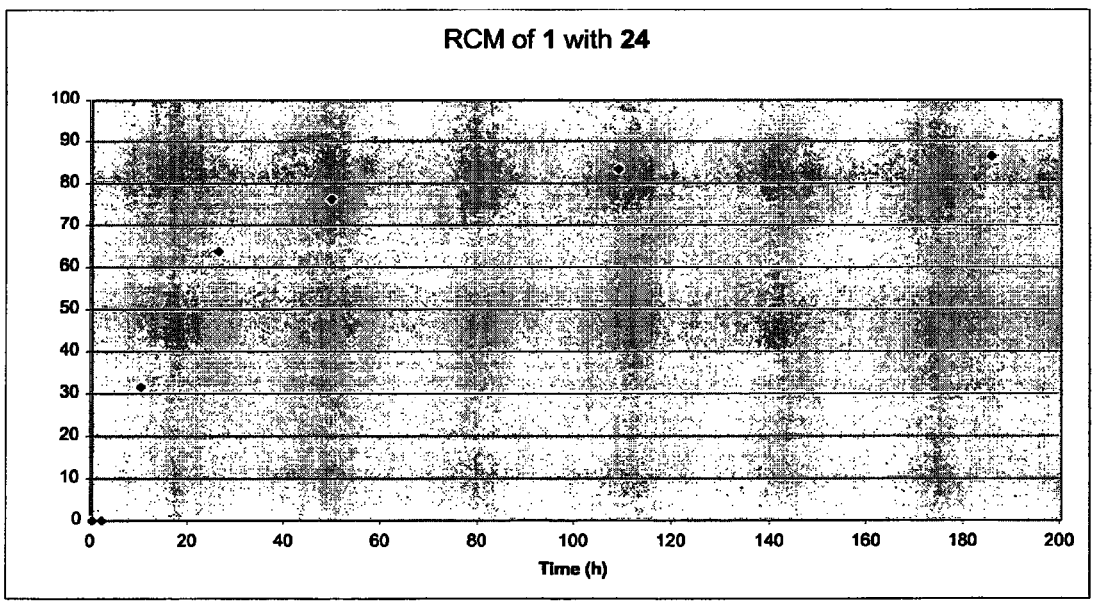
FIG. 9 shows the graph of conversion over time for the ring-closing metathesis of 1 with catalyst 24 described in Example 19.

In a glove box, 0.67 ml of stock solution X (3 mg of 24, 0.004 mmol) was transferred to a screw cap NMR tube. $CD_2Cl_2$ (0.13 ml) was added and then 1 (21.5 μl, 0.08 mmol). The NMR tube was sealed, removed from the glove box and heated to 30° C. FIG. 9 shows the graph of conversion over time.

Figure 10:
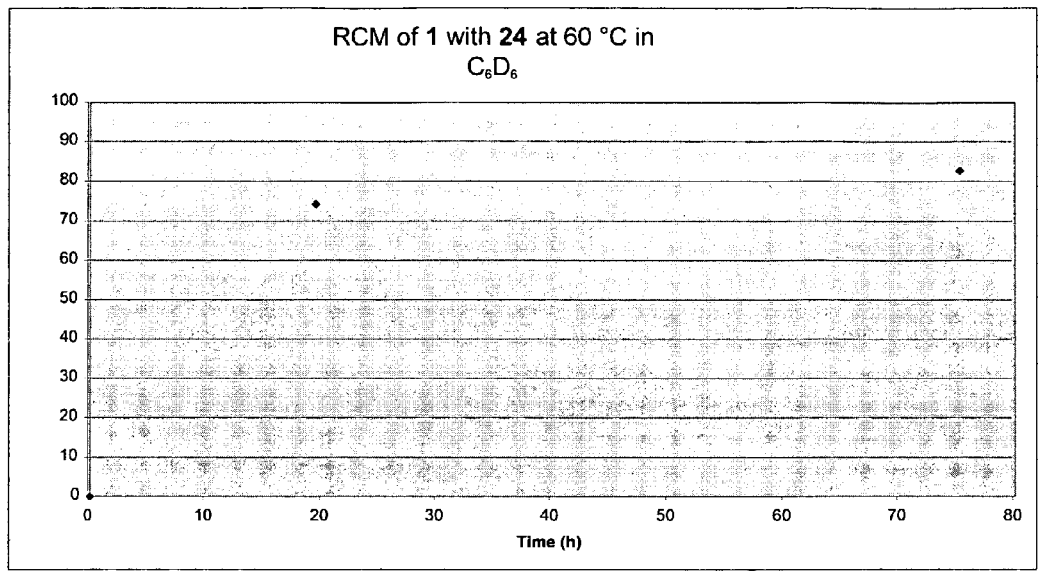
FIG. 10 is a graph of conversion over time for the ring-closing metathesis of 1 with catalyst 24 in $C_6D_6$, described in Example 19.

This experiment was repeated in $C_6D_6$ at 60° C. to examine the impact of temperature. Catalyst 24 (3 mg, 0.004 mmol) and $C_6D_6$ (0.8 ml) were combined in a screw cap NMR tube and 1 (21.5 μl, 0.08 mmol) was added. The NMR tube was sealed, removed from the glove box and heated to 60° C. FIG. 10 is a graph of conversion over time in $C_6D_6$.

Example 20

RCM Activity with Less Hindered Olefins

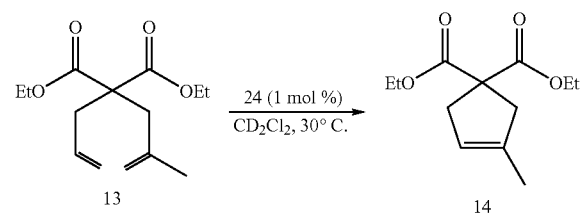

Figure 11:
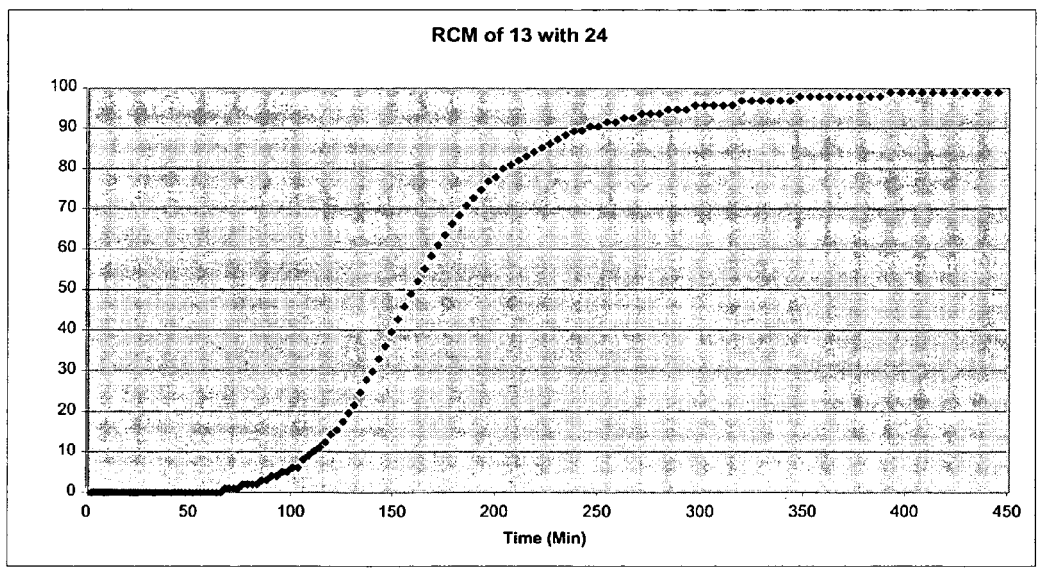
FIG. 11 is a graph of conversion over time for the ring-closing metathesis of 13 with catalyst 24 described in Example 20.

In a glove box, 0.8 ml of stock solution W (0.6 mg of 24, 0.0008 mmol) was transferred to a screw cap NMR tube. The NMR tube was sealed and transferred to a 500 MHz NMR which was warmed to 30° C. The NMR tube was then ejected, 13 (20.5 μl, 0.08 mmol) was added and the tube was injected for data collection. FIG. 11 is a graph of the conversion over time.

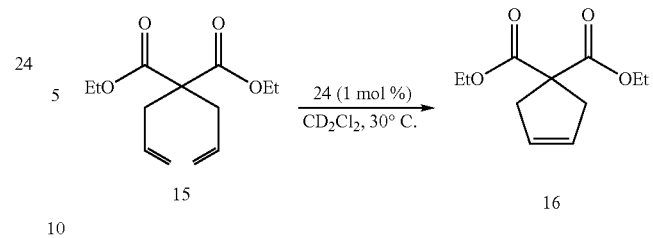

Figure 12:
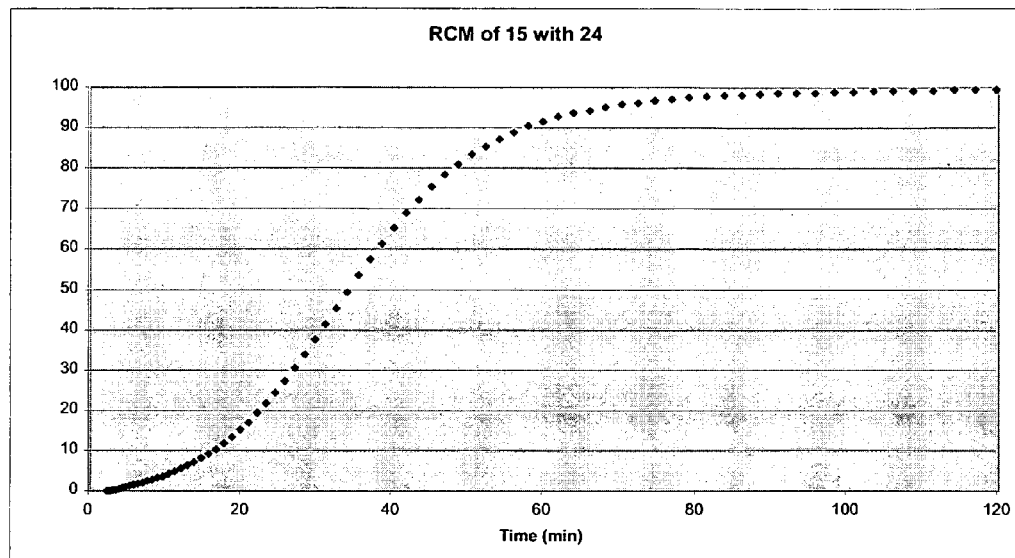
FIG. 12 is a graph of the conversion over time for the ring-closing metathesis of 15 with catalyst 24 described in Example 20.

In a glove box, 0.8 ml of stock solution W (0.6 mg of 24, 0.0008 mmol) was transferred to a screw cap NMR tube. The NMR tube was sealed and transferred to a 500 MHz NMR which was warmed to 30° C. The NMR tube was then ejected, 15 (19.5 μl, 0.08 mmol) was added and the tube was injected for data collection. FIG. 12 is a graph of the conversion over time.

Example 21

Activity Studies

Catalyst 25.

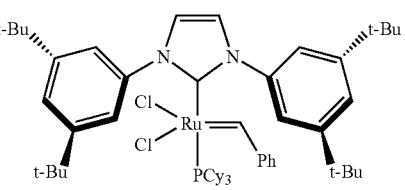

Preparation of stock solutions. Catalyst 25 (11 mg) was placed in a 2 ml volumetric flask and taken into a glove box. In the glove box, 2 ml of $CD_2Cl_2$ was added to make stock solution V. 0.4 ml of V was then transferred to another 2 ml volumetric flask and diluted to 2 ml with $CD_2Cl_2$ to make stock solution U.

Reaction Scheme 25

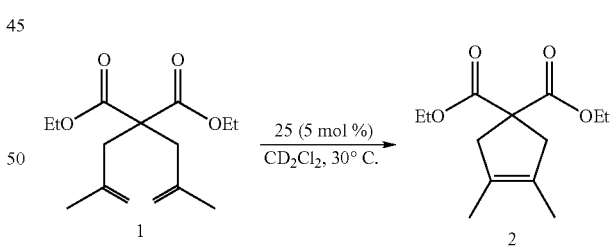

Figure 13:
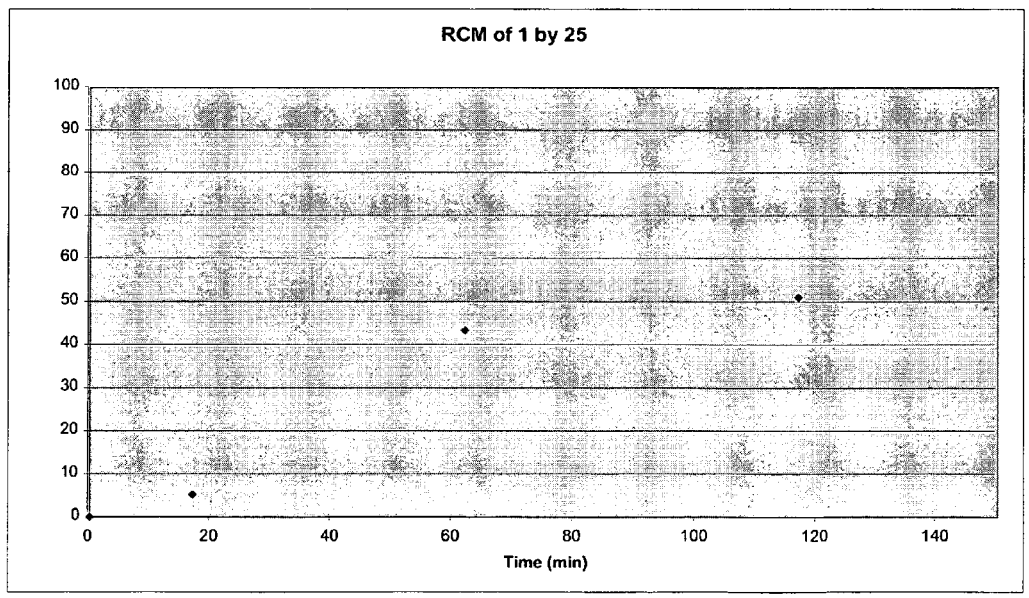
FIG. 13 is a graph of conversion over time for the ring-closing metathesis of 1 with catalyst 25 described in Example 21.

In a glove box, 0.55 ml of stock solution V (3 mg of 25, 0.003 mmol) was transferred to a screw cap NMR tube. $CD_2Cl_2$ (0.25 ml) was added and then 1 (21.5 μl, 0.08 mmol). The NMR tube was sealed, removed from the glove box and heated to 30° C. A graph conversion over time is shown in FIG. 13. No further conversion is observed after 2 hours.

Figure 14:
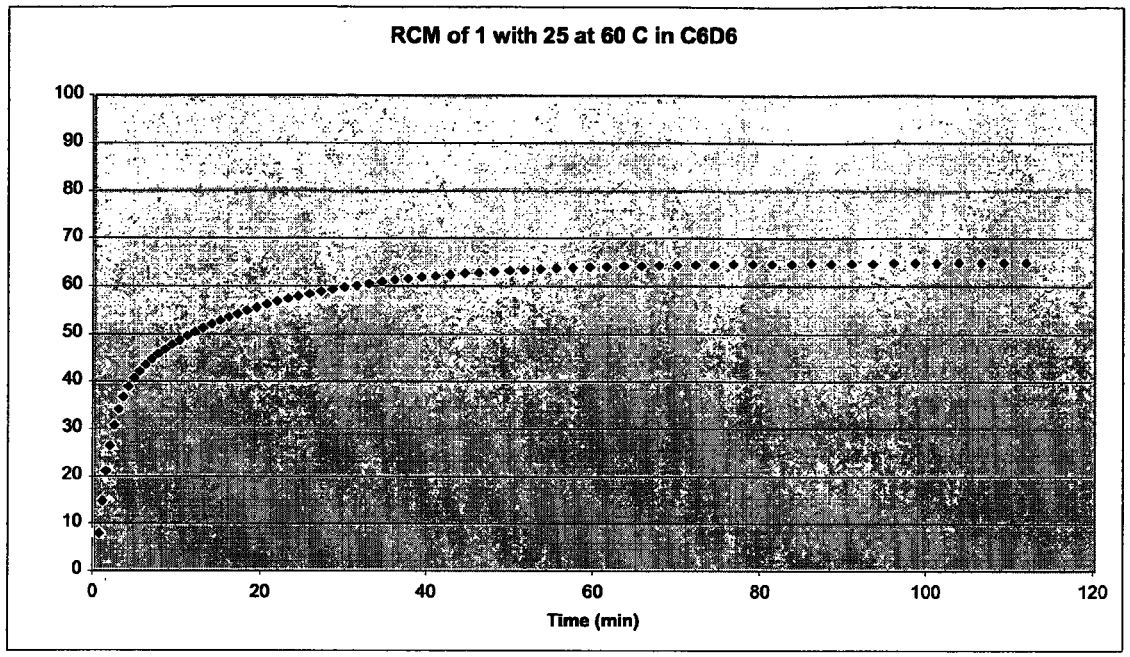
FIG. 14 is a graph of the conversion over time for the ring-closing metathesis of 1 with catalyst 25 in $C_6D_6$ described in Example 21.

This experiment was repeated in $C_6D_6$ at 60° C. to examine the impact of temperature. Catalyst 25 (3 mg, 0.003 mmol) and $C_6D_6$ (0.8 ml) were combined in a screw cap NMR tube and 10 (21.5 μl, 0.08 mmol) was added. The NMR tube was sealed and transferred to a 500 MHz NMR which was warmed to 60° C. The NMR tube was then ejected, 1 (21.5 μl, 0.08 mmol) was added and the tube was injected for data collection. FIG. 14 is a graph of the conversion over time.

Example 22

Activity Studies with Less Hindered Olefins

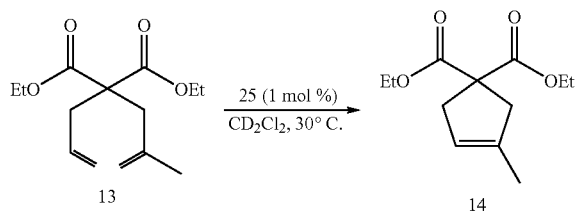

Figure 15:
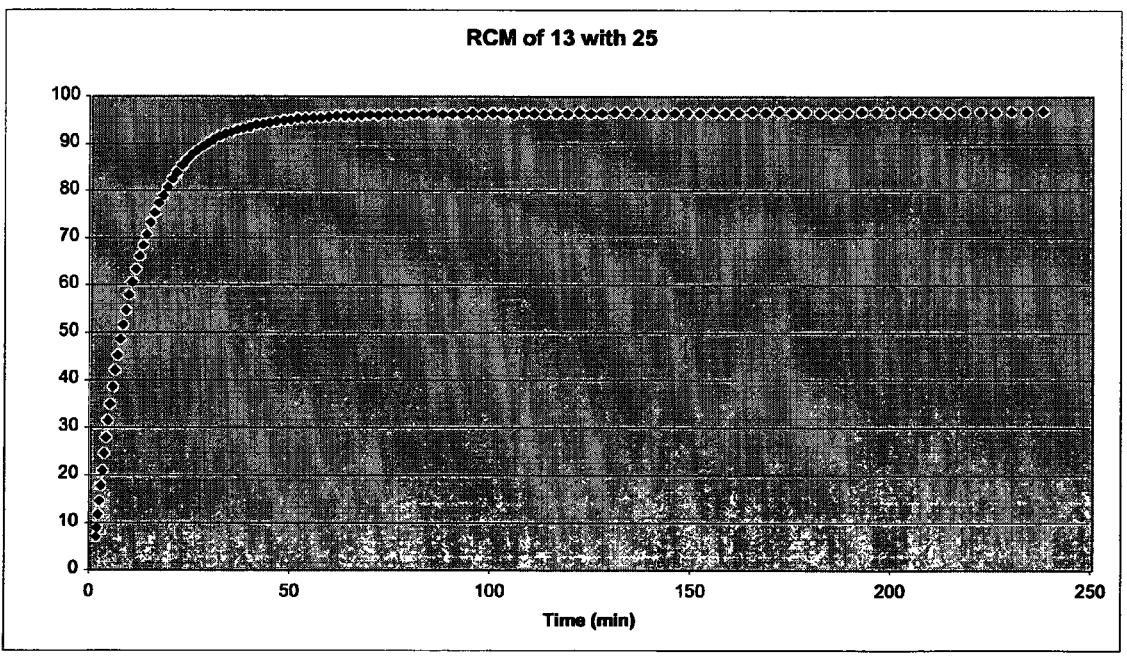
FIG. 15 is a graph of the conversion over time for the ring-closing metathesis of 13 with catalyst 25 described in Example 22.

In a glove box, 0.55 ml of stock solution U (0.6 mg of 25, 0.0008 mmol) was transferred to a screw cap NMR tube and 0.25 ml of CD$_2$Cl$_2$ was added. The NMR tube was sealed and transferred to a 500 MHz NMR which was warmed to 30° C. The NMR tube was then ejected, 13 (20.5 µl, 0.08 mmol) was added and the tube was injected for data collection. FIG. 15 is a graph of the conversion over time.

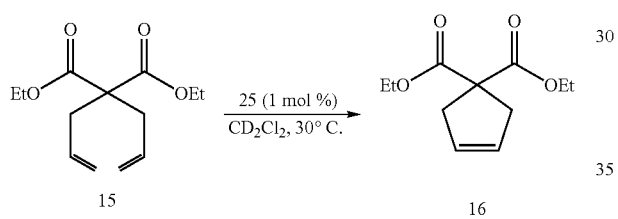

Figure 16:
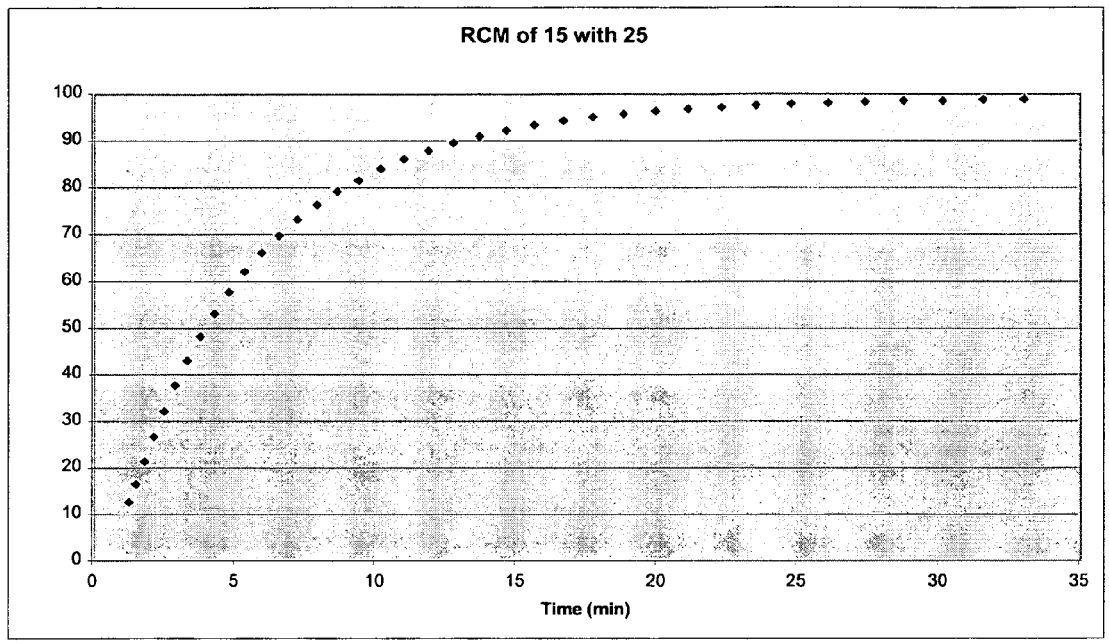
FIG. 16 is a graph of the conversion over time for the ring-closing metathesis of 15 with catalyst 25 described in Example 22.

In a glove box, 0.55 ml of stock solution U (0.6 mg of 25, 0.0008 mmol) was transferred to a screw cap NMR tube and 0.25 ml of CD$_2$Cl$_2$ was added. The NMR tube was sealed and transferred to a 500 MHz NMR which was warmed to 30° C. The NMR tube was then ejected, 15 (19.5 µl, 0.08 mmol) was added and the tube was injected for data collection. FIG. 16 is a graph of the conversion over time.

Example 23

Activity Study

Catalyst 26.

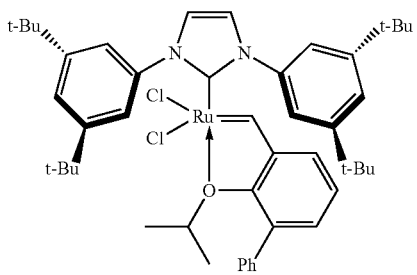

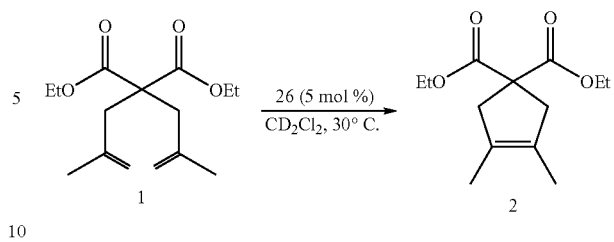

Figure 17:
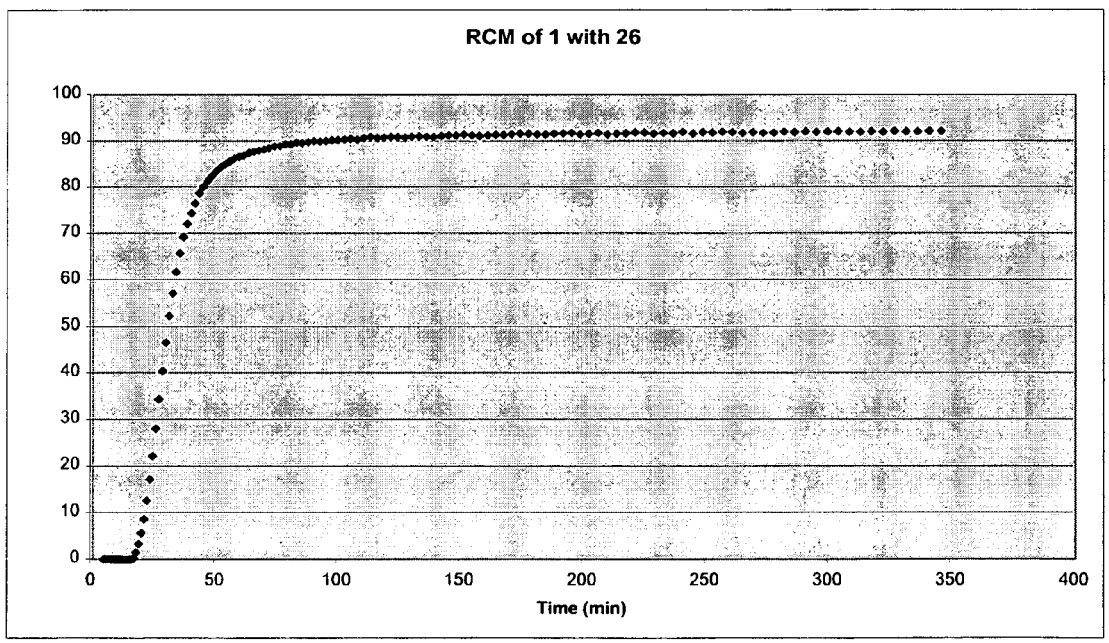
FIG. 17 is a graph of the conversion over time for the ring-closing metathesis of 1 with catalyst 26 described in Example 23.

In a glove box, catalyst 26 (2 mg, 0.002 mmol) was combined with CD$_2$Cl$_2$ (0.4 ml) in a screw cap NMR tube. The NMR tube was sealed and transferred to a 500 MHz NMR which was warmed to 30° C. The NMR tube was then ejected, 1 (11 µl, 0.04 mmol) was added and the tube was injected for data collection. FIG. 17 is a graph of the conversion over time that illustrates the dramtic decrease in reaction time necessary, relative to catalyst 12, for catalyst 26 to give 90% conversion of 1 to 2.

Example 24

Activity of Catalysts 6a, 6c, 27a and 27c in the Ring-Closing Metathesis of Dimethyl 2,2-di(2-methylallyl)malonate

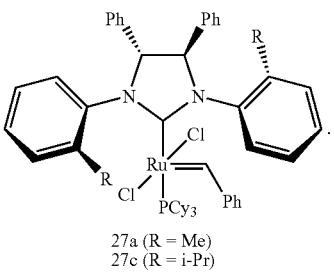

27a (R = Me)
27c (R = i-Pr)

Figure 18:
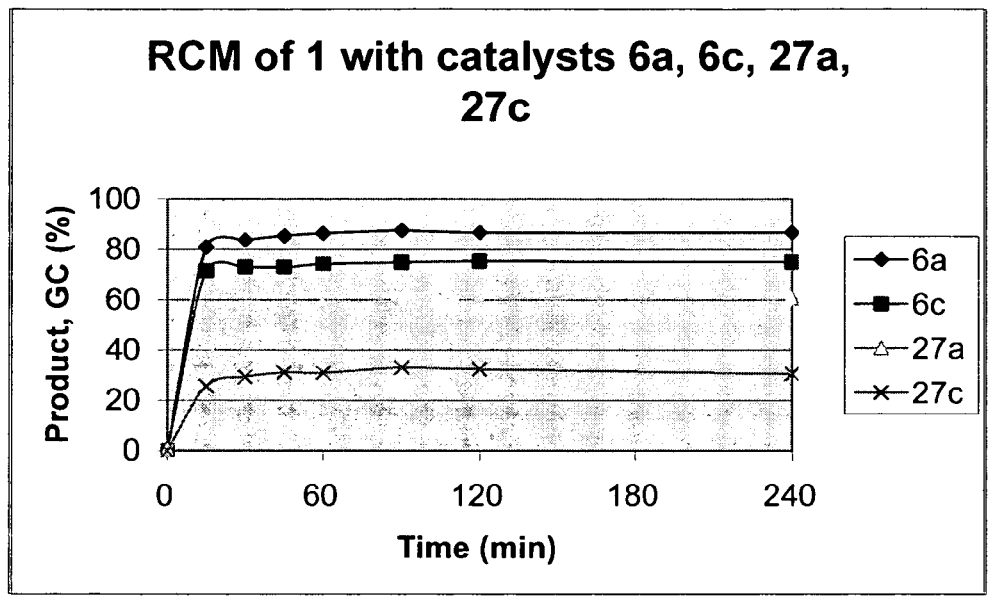
FIG. 18 shows the conversion over time for the ring-closing metathesis of 1 with catalyst 6a, 6c, 27a and 27c described in Example 24.

The procedure used was the same as that described in Example 3 using catalysts 27a and 27c. The results for 6a, 6c, 27a and 27c are shown in FIG. 18. The results shown in FIG. 18 demonstrate that catalysts 6a and 6c perform better than 27a and 27c in the ring-closing metathesis of dimethyl 2,2-di(2-methylallyl)malonate. These results indicate that a catalyst based on an NHC ligand that has an unsubstituted bridge between the nitrogen atoms performs better than a catalyst that has phenyl substitutents on each carbons of that same bridge.

Example 25

Ring-Closing Metathesis of Dimethyl 2,2-di(2-methylallyl)malonate Using 5 mol % of Catalysts 6a and 7a in Toluene at 40° C. and 60° C.

Figure 19:
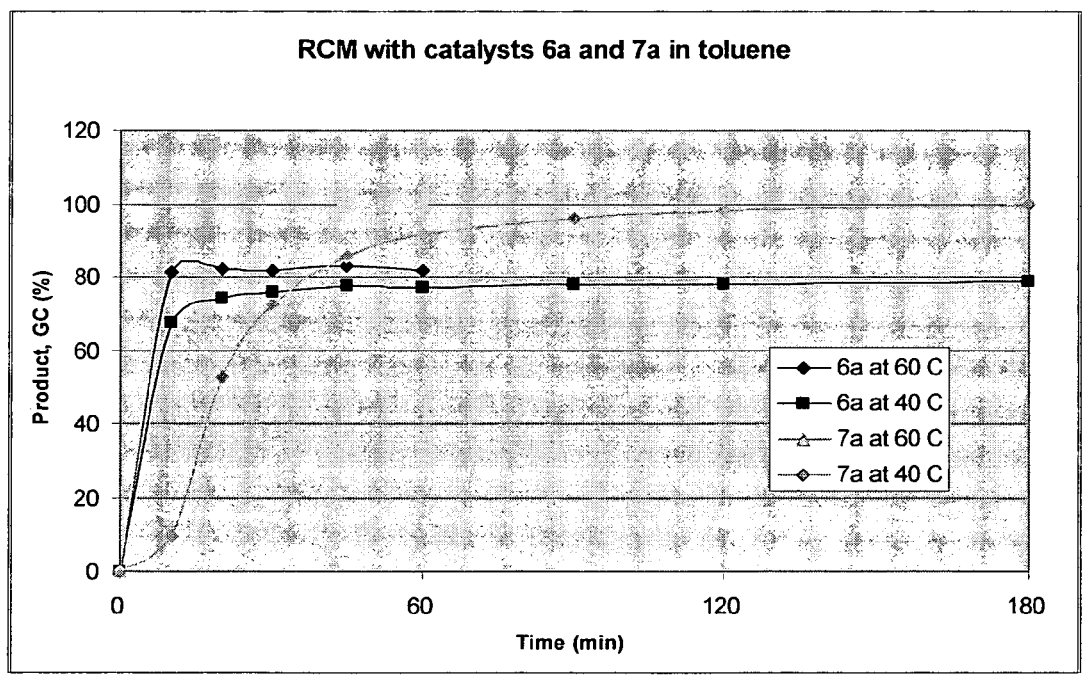
FIG. 19 shows the conversion over time for the ring-closing metathesis of 1 with catalyst 6a and 7a in toluene described in Example 25.

A procedure analogous to that described in Example 3 was used, except that methylene chloride was replaced with toluene. The results are shown in FIG. 19.

Example 26

Catalyst 12 and catalyst B were compared under identical reaction conditions for the production of tetrasubstituted olefins by RCM. The reactions were performed with 0.08 mmol of substrate, 0.004 mmol of catalyst, 0.8 ml of C$_6$D$_6$ at 60° C. A comparison table follows.

TABLE 15

RCM to form tetrasubstituted olefins. NR = no reaction.

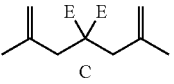

Conversions (isolated yields) with catalysts

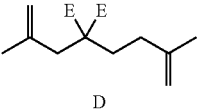

| Substrate (E = CO$_2$Et) | B | 12 |
|---|---|---|
| 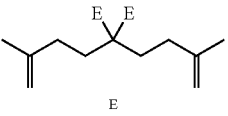 C | 30 | 93 (86) |
| 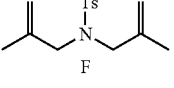 D | >95 | >95 (99) |
| E | 50 | 51 (47) |
| F | 85 | >95 (99) |
| 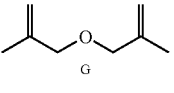 G | >95 | >95 |
| 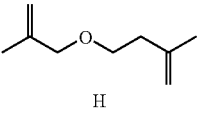 H | 43[1] | 78[2] |

[1] 75% consumption of H.
[2] 10% 2,6-dichlorobenzoquinone added. Without 2,6-dichlorobenzoquinone: 60% conversion to product, 95% consumption of H.

Two of these substrates, D and G, were completely converted to product with both catalysts. Catalyst 12 gave improved conversion relative to catalyst B for every other substrate except E. Substrate H warrants further discussion. Use of catalyst B gave a mixture of three compounds, with 43% conversion to product, 32% conversion to a rearranged byproduct and 25% remaining starting material (H). Use of catalyst 12 resulted in complete consumption of H, but with only 60% conversion to product and 40% conversion to the byproduct. Interestingly, catalyst 10 gave 43% conversion to the product and no byproduct formation. Ruthenium hydride species formed from the decomposition of ruthenium olefin metathesis catalysts are known to catalyze the migration of olefins at 40° C. in CD$_2$Cl$_2$. Hong, S. H.; Day, M. W.; Grubbs, R. H. *J. Am. Chem. Soc.* 2004, 126, 7414. Repeating the reactions using B and 12 with 10% 2,6-dichloroquinone added to consume any hydride formed, (Hong, S. H.; Sanders, D. P.; Lee, C. W.; Grubbs, R. H. *J. Am. Chem. Soc.* 2005, 127, 17160) catalyst B gave very poor conversion, but catalyst 12 gave 78% conversion to product with no byproduct formation. Overall, catalyst 12 performed as well as or better than B for all of the substrates.

Example 26

Comparison of Catalysts A, 12 and 7a in Different Ring-Closing Metathesis Reactions to Form Tetrasubstituted Olefins A procedure similar to that described in Example 8 was used to set up the ring-closing metathesis reactions and to follow their progress. The results are summarized in Table 16.

TABLE 16

RCM to form tetrasubstituted olefins (E = $CO_2Et$; Ts = tosyl). NR = no reaction.

| Substrate | Conversions (isolated yields) [%] with catalysts C848, 12, and 7a | | |
|---|---|---|---|
| | A | 12 | 7a |
| C | 30 | 93 (86) | >95 |
| D | >95 | >95 (99) | >95 |
| E | 50 | 51 (47) | 62 |
| F | 85 | >95 (99) | >95 |
| G | >95 | >95 | >95 |
| H | 43[a] | 78[b] | 88 |

[a] 75% consumption of 17.
[b] 10% 2,6-dichlorobenzoquinone added. Without 2,6-dichlorobenzoquinone: 60% conversion to product, 95% consumption of 17.

Example 27

Cross Metathesis (CM) Results with Catalyst 7a

General procedure for CM reactions. A reflux condenser was attached to a flame-dried 10 mL 2-neck round bottom flask and the apparatus was flushed with argon. The flask was charged with solid catalyst and a stir bar. The second neck was closed with a septum, and dry, degassed $C_6H_6$ (2.5 mL) was added via syringe. The reagents were then added simultaneously via syringe. The solution was heated to 60° C. using an oil bath, and was stirred under argon for 18 h. The solution was then cooled to room temperature and concentrated. Conversions were measured by $^1H$ NMR of this crude reaction mixture, and yields determined by isolating the desired products by silica gel column chromatography.

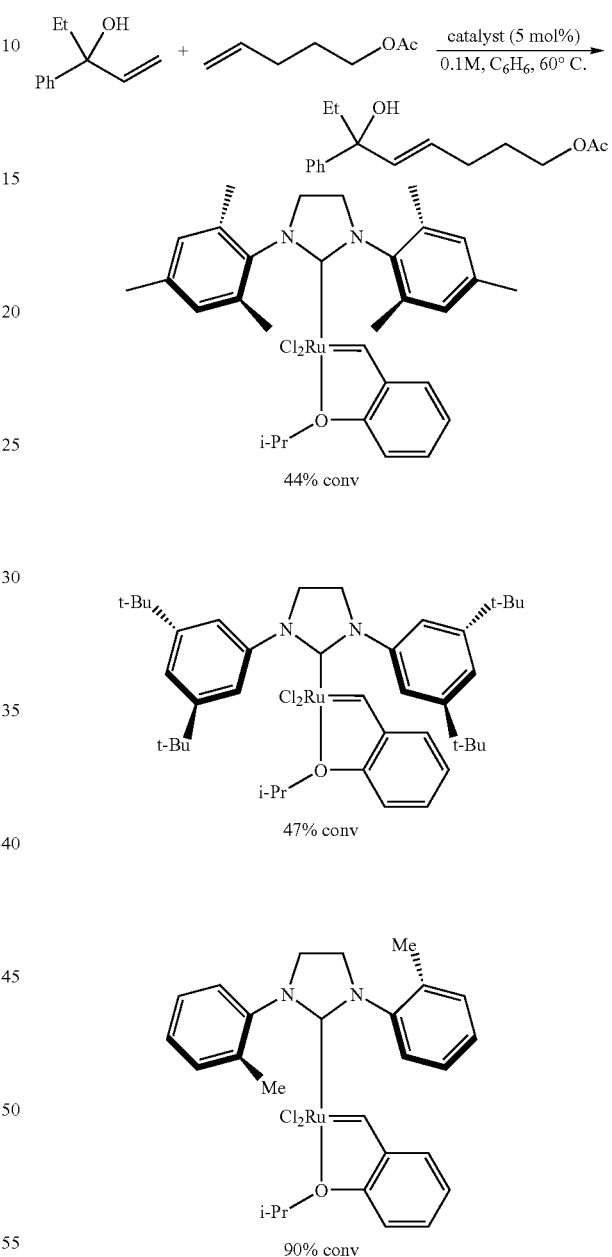

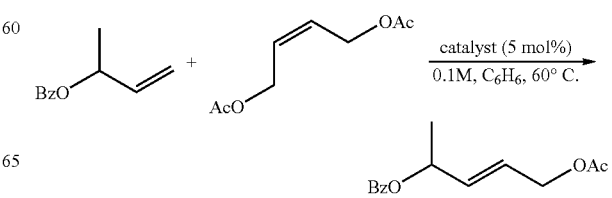

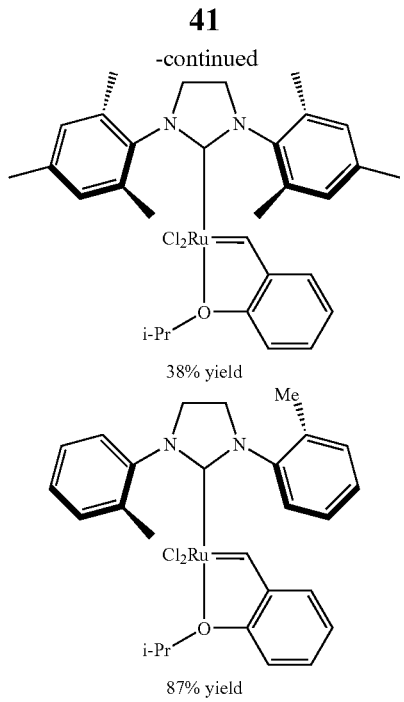

38% yield

87% yield

Example 28

Preparation of bis(pyridine) Catalyst 28

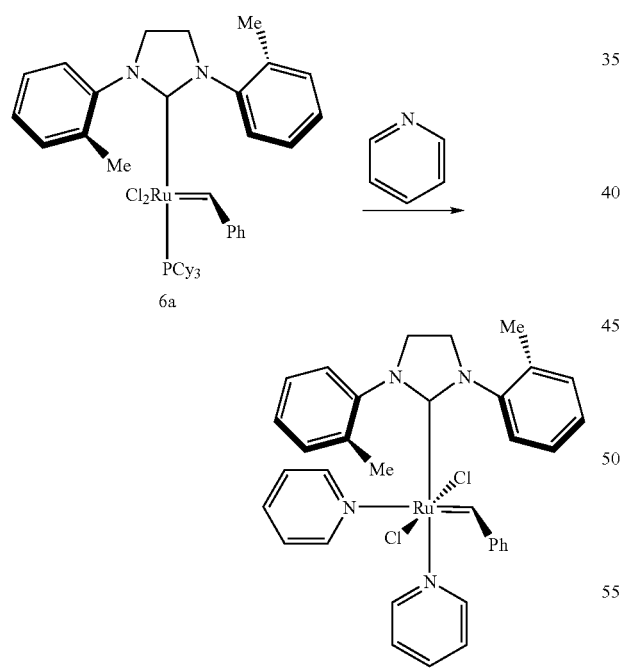

In a nitrogen-filled glove box, pyridine (3.0 mL) was added to catalyst 6a (0.1 g, 0.126 mmol) and the solution was stirred until all of 6a had dissolved. The desired product was isolated by precipitation with pentane (0.070 g, 0.104 mmol, 83% yield). Green crystalline solid. $^1$H NMR (300 MHz, $C_6D_6$): δ 19.30 (s), 9.51 (d), 8.53 (m), 7.92 (d), 7.25-7.05 (m), 7.00-6.77 (m), 6.64 (m), 6.51 (t), 6.22 (t), 3.08-3.64 (m), 2.49 (s), 2.31 (s).

Example 29

Ring-Closing Metathesis Reactions Using Catalysts 6a and 7a

Figure 20:
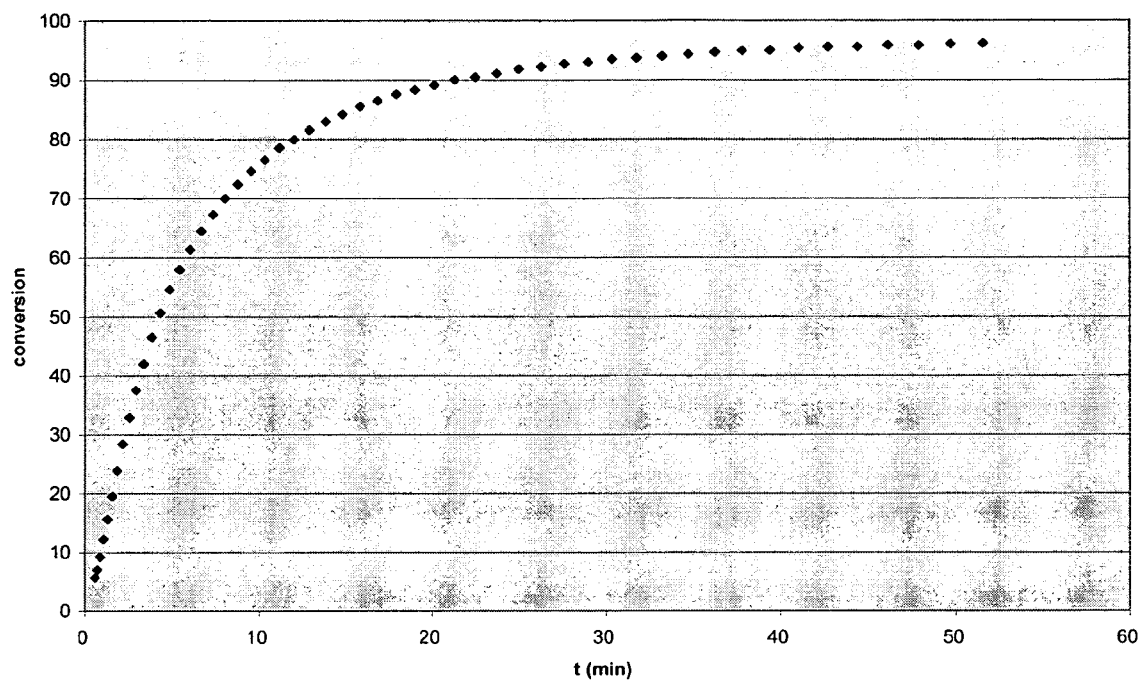
Figure 21:
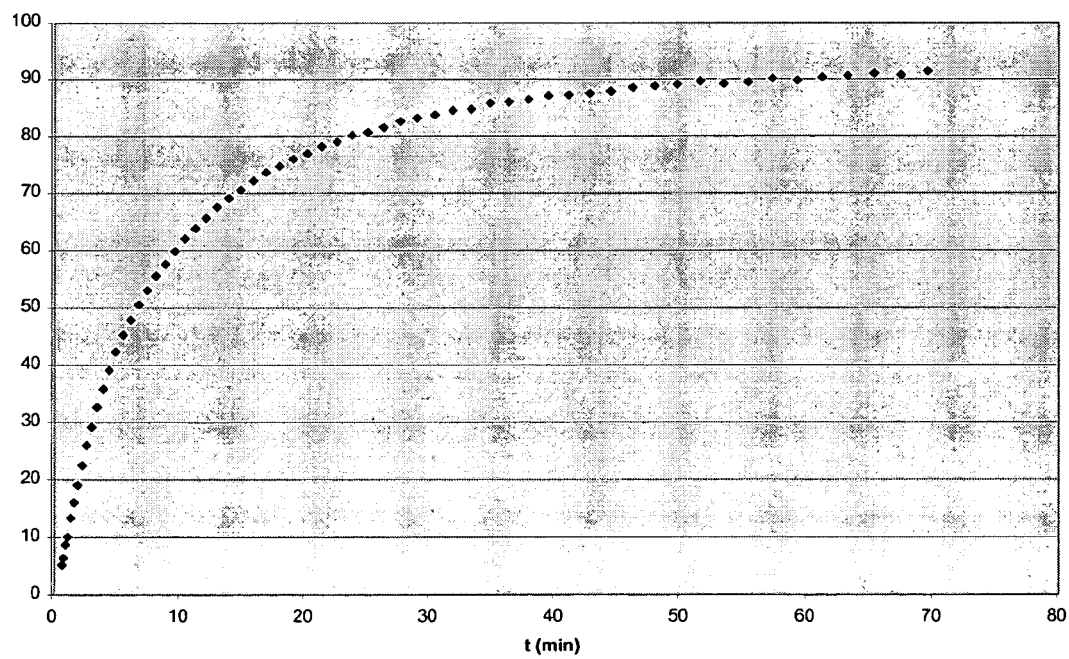
Figure 22:
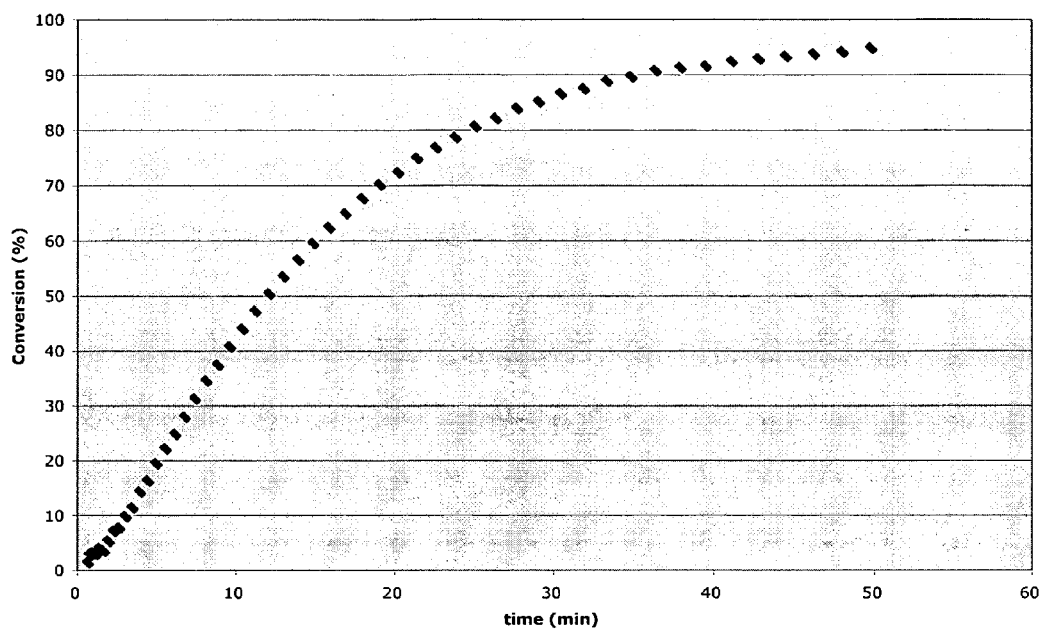
Figure 23:
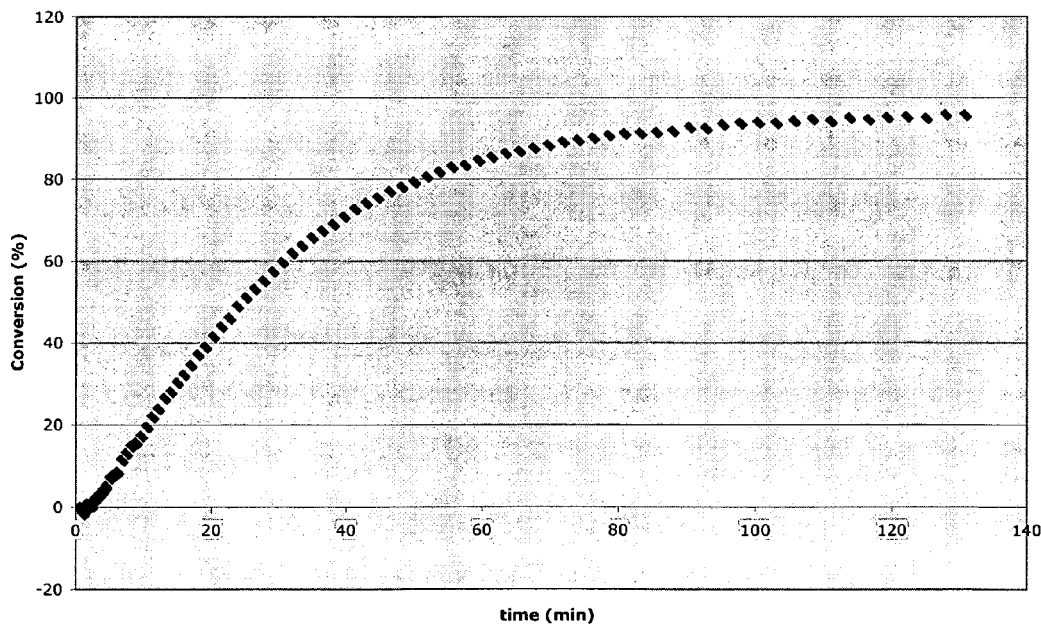

The ring-closing reactions described in Example 22 were repeated using catalysts 6a and 7a with of substrates 13 and 15 to form the corresponding di- and tri-substituted olefins. The results are shown in FIGS. 20-23. FIG. 20 is a graph of the conversion of 15 over time for the RCM reaction for catalyst 6a. FIG. 21 is a graph of the conversion of 13 over time for the RCM reaction for catalyst 6a. FIG. 22 is a graph of the conversion of 15 over time for the RCM reaction for catalyst 7a. FIG. 23 is a graph of the conversion of 13 over time for the RCM reaction for catalyst 7a.

The claimed invention is:

1. An N-heterocyclic carbene (NHC) ruthenium olefin metathesis catalyst of formula (I):

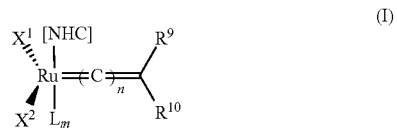

wherein:
$X^1$ and $X^2$ are independently anionic ligands;
n is 0, 1 or 2;
$R^9$ and $R^{10}$ are each independently hydrogen or a substituted or unsubstituted substituent selected from the group consisting of $C_1$-$C_{20}$ alkyl, $C_2$-$C_{20}$ alkenyl, $C_2$-$C_{20}$ alkynyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl; or $R^9$ and $R^{10}$ may optionally be linked together to form a cyclic structure via one of the listed substituents;
m is 1 or 2;
when m is 1, L is a neutral 2-electron donor ligand and may optionally be linked to $R^{10}$ forming a chelating carbene ligand when n is zero;
when m is 2, L is a heteroarene ligand; and
NHC is an N-heterocyclic carbene ligand selected from formulas (III)-(V):

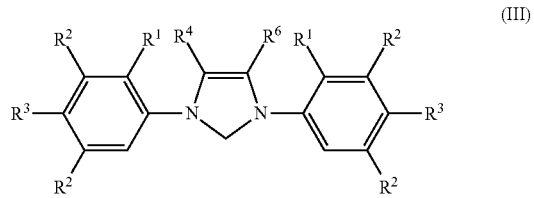

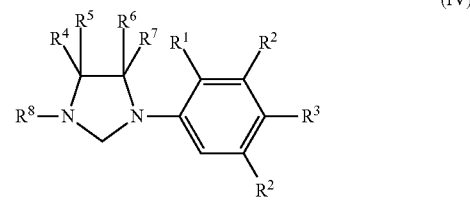

-continued (V)

[Structure showing imidazoline ring with R⁴, R⁶, R¹, R², R⁸, R³ substituents]

wherein
$R^1$, $R^2$, and $R^3$ are either:
a) each $R^1$ is independently a primary or secondary $C_1$-$C_4$ alkyl group; each $R^2$ is independently H, a substituted or unsubstituted $C_1$-$C_{10}$ alkyl group, substituted or unsubstituted phenyl, substituted or unsubstituted naphthyl, or substituted or unsubstituted anthracenyl; and each $R^3$ is independently H, a substituted or unsubstituted $C_1$-$C_8$ alkyl group, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; or
b) $R^1$ is H; each $R^2$ is independently H, a substituted or unsubstituted $C_1$-$C_8$ alkyl group, substituted or unsubstituted phenyl, substituted or unsubstituted naphthyl, or substituted or unsubstituted anthracenyl; and each $R^3$ is independently H, a substituted or unsubstituted $C_1$-$C_8$ alkyl group, substituted or unsubstituted phenyl, substituted or unsubstituted naphthyl, or substituted or unsubstituted anthracenyl or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; with the provisos that both $R^2$ substituents on the same phenyl ring are not H;

$R^4$ and $R^6$ are each independently H, a substituted or unsubstituted $C_1$-$C_8$ alkyl group, substituted or unsubstituted aryl, or in formulas (III) and (V), together with the carbons carrying them, form a substituted or unsubstituted, fused 4-8 membered carbocyclic ring or a substituted or unsubstituted, fused aromatic ring;

$R^5$ and $R^7$ are independently H, a substituted or unsubstituted $C_1$-$C_8$ alkyl group; and $R^8$ is a $C_1$-$C_{12}$ alkyl or a $C_3$-$C_{12}$ cycloalkyl.

2. An N-heterocyclic carbene (NHC) ruthenium olefin metathesis catalyst according to claim 1, wherein the NHC ligand is selected from the group consisting of

[Structure: imidazole with two ortho-R¹-phenyl groups]

where $R^1$ is methyl, ethyl, propyl, or isopropyl;

[Structure: imidazole with two 3,5-R²-phenyl groups]

where $R^2$ is tert-butyl;

[Structure: imidazoline with R⁶, R⁷, R¹, R⁸ substituents and phenyl]

and where $R^1$ is methyl, ethyl, propyl, or isopropyl; $R^6$ and $R^7$ are hydrogen or methyl; and $R^8$ is methyl;

[Structure: imidazole with R⁸, R¹ substituents]

where $R^1$ is methyl, ethyl, propyl, or isopropyl; and $R^8$ is methyl.

3. An N-heterocyclic carbene (NHC) ruthenium olefin metathesis catalyst according to claims 1 or 2, wherein:
$X^1$ and $X^2$ are halide, or a substituted or unsubstituted group selected from the group consisting of benzoate, $C_1$-$C_5$ carboxylate, $C_1$-$C_5$ alkyl, phenoxy, $C_1$-$C_5$ alkoxy, $C_1$-$C_5$ alkylthio, aryl, and $C_1$-$C_5$ alkyl sulfonate;
n is 0 or 1;
$R^9$ is hydrogen, $C_1$-$C_5$ alkyl or aryl;
$R^{10}$ is a substituted or unsubstituted group selected from the group consisting of $C_1$-$C_{20}$ alkyl, $C_2$-$C_{20}$ alkenyl, and aryl;
m is 1; and
L is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether, or is linked to $R^{10}$ forming a chelating carbene ligand when n is 0.

4. An N-heterocyclic carbene (NHC) ruthenium olefin metathesis catalyst according to claim 3, wherein:
$X^1$ and $X^2$ are each halide, $CF_3CO_2$, $CH_3$, $CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate;
n is 0 or 1;
$R^9$ is hydrogen, $C_1$-$C_5$ alkyl or aryl;
$R^{10}$ is a substituted or unsubstituted group selected from the group consisting of $C_1$-$C_{20}$ alkyl, $C_2$-$C_{20}$ alkenyl, and aryl;
m is 1; and
L is a phosphine of the formula PR'R"R'", where R', R", and R'" are each independently aryl, $C_1$-$C_{10}$ alkyl, or $C_3$-$C_6$ cycloalkyl, or is linked to $R^{10}$ forming a chelating carbene ligand when n is 0.

5. An N-heterocyclic carbene (NHC) ruthenium olefin metathesis catalyst according to claim 4, wherein:
$X^1$ and $X^2$ are each chloride;
n is 0;
$R^9$ is hydrogen;
$R^{10}$ is phenyl, vinyl or $-C=C(CH_3)_2$;
m is 1; and L is selected from the group consisting of P(cyclohexyl)$_3$, P(cyclopentyl)$_3$, P(isopropyl)$_3$, and P(phenyl)$_3$, or is linked to R$^{10}$ forming a chelating carbene ligand.

6. An N-heterocyclic carbene (NHC) ruthenium olefin metathesis catalyst according to claim 5, wherein the catalyst of formula (I) is selected from the group consisting of:

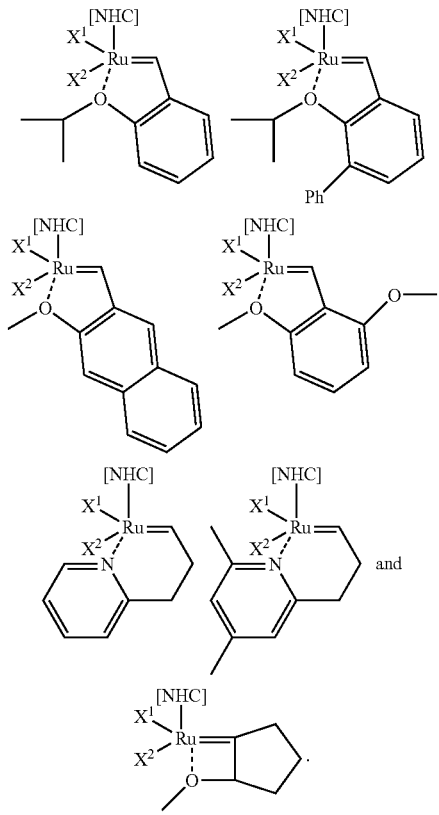

7. An N-heterocyclic carbene (NHC) ruthenium olefin metathesis catalyst according to claim 3, wherein the catalyst of formula (I) is selected from the group consisting of:

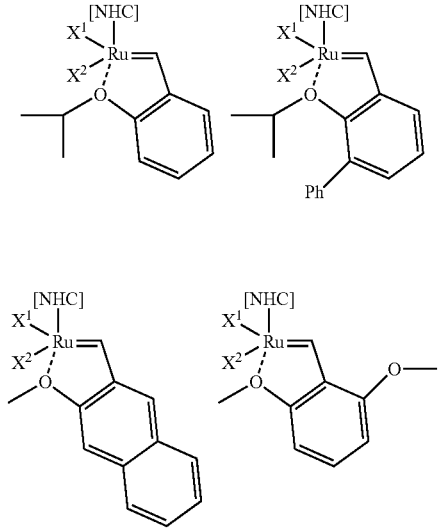

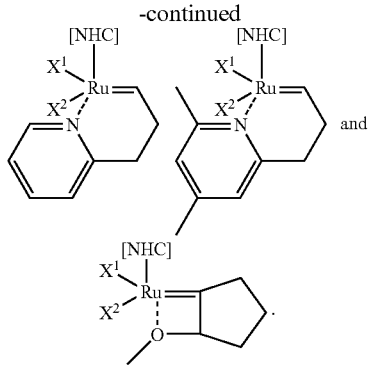

8. An N-heterocyclic carbene (NHC) ruthenium olefin metathesis catalyst according to claim 5, wherein L is selected from the group consisting of P(cyclohexyl)$_3$, P(cyclopentyl)$_3$, P(isopropyl)$_3$, and P(phenyl)$_3$.

9. An N-heterocyclic carbene (NHC) ruthenium olefin metathesis catalyst according to claim 3, wherein L is selected from the group consisting of P(cyclohexyl)$_3$, P(cyclopentyl)$_3$, P(isopropyl)$_3$, and P(phenyl)$_3$.

10. An N-heterocyclic carbene (NHC) ruthenium olefin metathesis catalyst selected from the group consisting of:

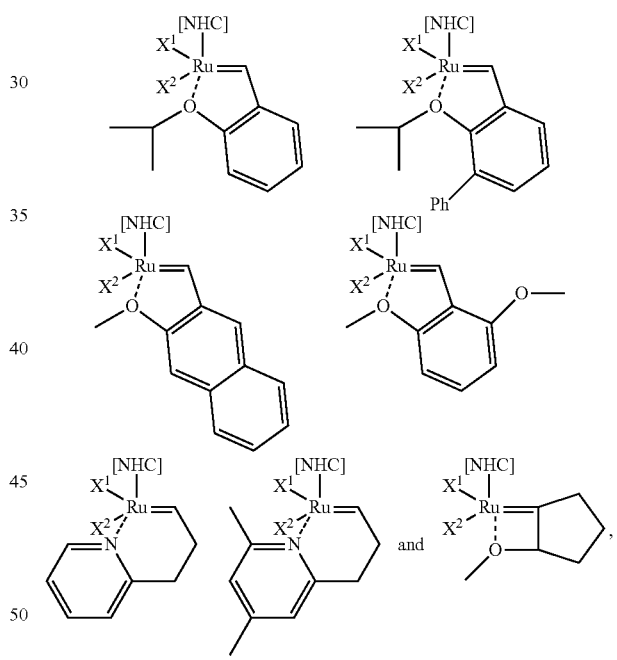

wherein:
X$^1$ and X$^2$ are independently anionic ligands;
n is 0, 1 or 2; and
NHC is an N-heterocyclic carbene ligand comprising a 5-membered heterocyclic ring having a carbenic carbon atom and at least one nitrogen atom contained within the 5-membered heterocyclic ring, wherein the nitrogen atom is directly attached to the carbenic carbon atom and is substituted by a phenyl ring, and wherein the phenyl ring has a hydrogen at either or both ortho positions and is substituted at at least one ortho or meta position.

11. An N-heterocyclic carbene (NHC) ruthenium olefin metathesis catalyst according to claim 10, wherein the NHC ligand is selected from a ligand of formula of formulas (II)-(V):

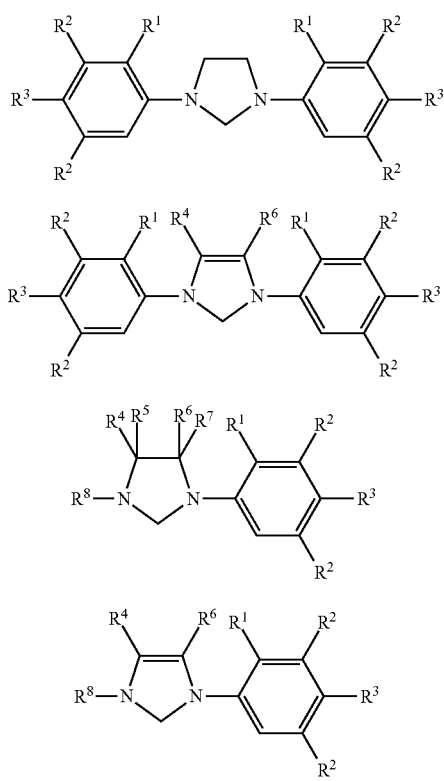

wherein
$R^1$, $R^2$, and $R^3$ are either:
a) each $R^1$ is independently a primary or secondary $C_1$-$C_4$ alkyl group; each $R^2$ is independently H, a substituted or unsubstituted $C_1$-$C_{10}$ alkyl group, substituted or unsubstituted phenyl, substituted or unsubstituted naphthyl, or substituted or unsubstituted anthracenyl; and
each $R^3$ is independently H, a substituted or unsubstituted $C_1$-$C_8$ alkyl group, substituted or unsubstituted phenyl, substituted or unsubstituted naphthyl, or substituted or unsubstituted anthracenyl, or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; or
b) $R^1$ is H; each $R^2$ is independently H, a substituted or unsubstituted $C_1$-$C_8$ alkyl group, substituted or unsubstituted phenyl, substituted or unsubstituted naphthyl, or substituted or unsubstituted anthracenyl; and each $R^3$ is independently H, a substituted or unsubstituted $C_1$-$C_8$ alkyl group, substituted or unsubstituted phenyl, substituted or unsubstituted naphthyl, or substituted or unsubstituted anthracenyl or a functional group selected from the group consisting of halo, hydroxyl, sulfhydryl, cyano, cyanato, thiocyanato, amino, nitro, nitroso, sulfo, sulfonato, boryl, borono, phosphono, phosphonato, phosphinato, phospho, phosphino, and silyloxy; with the provisos that both $R^2$ substituents on the same phenyl ring are not H;
$R^4$ and $R^6$ are each independently H, a substituted or unsubstituted $C_1$-$C_8$ alkyl group, substituted or unsubstituted aryl, or, in formulas (III) and (V), together with the carbons carrying them, form a substituted or unsubstituted, fused 4-8 membered carbocylic ring or a substituted or unsubstituted, fused aromatic ring;

$R^5$ and $R^7$ are independently H, a substituted or unsubstituted $C_1$-$C_8$ alkyl group; and
$R^8$ is a $C_1$-$C_{12}$ alkyl or a $C_3$-$C_{12}$ cycloalkyl.

12. An N-heterocyclic carbene (NHC) ruthenium olefin metathesis catalyst according to claim 11, wherein the NHC ligand is selected from the group consisting of

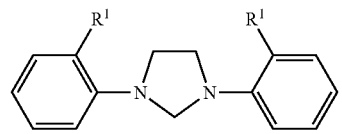

where $R^1$ is methyl, ethyl, propyl, or isopropyl;

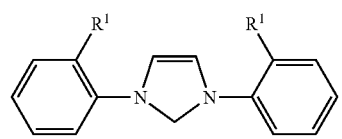

where $R^1$ is methyl, ethyl, propyl, or isopropyl;

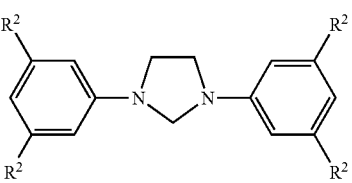

where $R^2$ is tert-butyl;

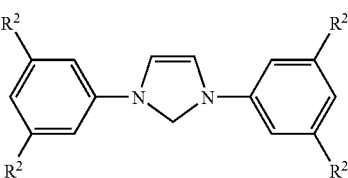

where $R^2$ is tert-butyl;

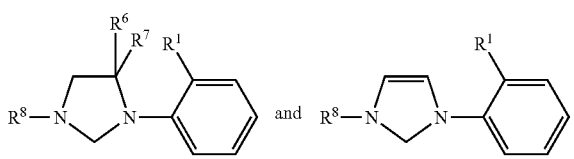

where $R^1$ is methyl, ethyl, propyl, or isopropyl; $R^6$ and $R^7$ are hydrogen or methyl; and $R^8$ is methyl;
where $R^1$ is methyl, ethyl, propyl, or isopropyl; and $R^8$ is methyl.

13. An N-heterocyclic carbene (NHC) ruthenium olefin metathesis catalyst according to claim 10, 11, or 12, wherein $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate.

14. An N-heterocyclic carbene (NHC) ruthenium olefin metathesis catalyst according to claim 13, wherein $X^1$ and $X^2$ are each chloride.

* * * * *